(12) United States Patent
Wintner et al.

(10) Patent No.: US 8,202,997 B2
(45) Date of Patent: Jun. 19, 2012

(54) COMPOSITIONS AND METHODS FOR TREATING OR PREVENTING HYPOXIC OR ISCHEMIC INJURY

(75) Inventors: Edward A. Wintner, Belmont, MA (US); Fuqiang Ruan, Bellevue, WA (US)

(73) Assignee: Ikaria, Inc., Hampton, NJ (US)

( * ) Notice: Subject to any disclaimer, the term of this patent is extended or adjusted under 35 U.S.C. 154(b) by 77 days.

(21) Appl. No.: 12/580,458

(22) Filed: Oct. 16, 2009

(65) Prior Publication Data

US 2010/0130555 A1    May 27, 2010

Related U.S. Application Data

(60) Provisional application No. 61/105,910, filed on Oct. 16, 2008.

(51) Int. Cl.
*C07D 213/62* (2006.01)
*C07D 263/30* (2006.01)
*C07D 321/00* (2006.01)

(52) U.S. Cl. .................. 546/261; 548/261; 568/22

(58) Field of Classification Search .................. 546/235; 548/22; 568/24, 25
See application file for complete search history.

(56) References Cited

U.S. PATENT DOCUMENTS 4,115,590 A    9/1978   Lerner
2008/0199541 A1   8/2008   Tomaselli et al.

OTHER PUBLICATIONS

Wolff, Manfred E. "Burger's Medicinal Chemistry, 5ed, Part I", John Wiley & Sons, 1995, pp. 975-977.*
Banker, G.S. et al, "Modem Pharmaceutics, 3ed.", Marcel Dekker, New York, 1996, pp. 451 and 596.*
Munday et al. (Food and Chemical Toxicology; 41; 1609-1615 (2003).*
Ahlemeyer, B., et al., "Testing Drug Effects against Hypoxic Damage of Cultured Neurons During Long-Term Recovery", vol. 45, No. 9, Jan. 1, 1989, pp. 835-842.
Macdonald, Justin A. et. al., "Structure-activity Relationships for Selected Sulfur-rich Antithrombotic Compounds" vol. 273, No. 2, Jul. 5, 2000, pp. 421-424.
Megn, Fan-Xue, et al., "The Effect of Phospholipase A2 inhibitor DTNB on the rat ischemia reperfusion arrhythmia", online, Chemical abstracts service, Columbus, OH, Jun. 22, 2000.
Rossoni, G. et al., "The Hydrogen Sulphide-releasing Derivative of Diclofenac Protects against Ischemia-reperfusion injury in the isolated rabbit heart", British Journal of Pharmacology, Nature Publishing Group, vol. 153, No. 1, Jan. 1, 2008, pp. 100-109.
Saletu, B., et al., "EEG Brain Mapping in Gerontopsychopharmacology on Protective Properties of Pyritinol against Hypoxic Hypoxidosis" Psychiatry Research, vol. 29, No. 3, 1989, pp. 387-390.
XP002582708, (online) Chemical Abstracts Service, Columbus, OH, Jul. 8, 2001.
XP002582711, (online) Chemical Abstracts Service, Columbus, OH, Nov. 16, 1984.

* cited by examiner

*Primary Examiner* — Brandon Fetterolf
*Assistant Examiner* — Shirley V Gembeh
(74) *Attorney, Agent, or Firm* — Diehl Servilla LLC

(57) ABSTRACT

A method for treating or preventing injury of a biological material exposed to hypoxic or ischemic conditions comprising contacting the biological material with an effective amount of a compound is disclosed. The compound has the following structure (I):

$$R^1-(S)_n-R^2 \qquad (I)$$

or a stereoisomer, pharmaceutically acceptable salt or prodrug thereof, wherein $R^1$, $R^2$, and n are as defined herein. Compounds, methods associated with preparation and use of such compounds, as well as pharmaceutical compositions comprising such compounds, are also disclosed.

7 Claims, 13 Drawing Sheets

US 8,202,997 B2

COMPOSITIONS AND METHODS FOR TREATING OR PREVENTING HYPOXIC OR ISCHEMIC INJURY

CROSS-REFERENCE TO RELATED APPLICATION

This application claims the benefit under 35 U.S.C. §119(e) of U.S. Provisional Patent Application No. 61/105,910, filed Oct. 16, 2008, which application is incorporated herein by reference in its entirety.

BACKGROUND OF THE INVENTION

1. Field of the Invention

The present invention is directed to methods for treating or preventing injury of a biological material exposed to hypoxic or ischemic conditions and to compounds and compositions comprising compounds useful for the same.

2. Description of the Related Art

Compounds containing a chalcogen element, i.e., those in Group 6 of the periodic table, but excluding oxides, are commonly termed "chalcogenides" or "chalcogenide compounds." These elements are sulfur (S), selenium (Se), tellurium (Te) and polonium (Po). Common chalcogenides contain one or more of S, Se, and Te, in addition to other elements.

It has been shown that treatment with chalcogenides protects biological matter from hypoxic and ischemic injury. In these studies, it was demonstrated that a stable composition of hydrogen sulfide ($H_2S$), a potent inhibitor of oxygen consumption, reduced hypoxic injuries in small and large animals (see U.S. Patent Application Publication No. 2008/0199541). Although hydrogen sulfide has not been typically considered for medical use, this unexpected result presents exciting possibilities for the treatment or prevention of a number of animal and human diseases, particularly hypoxia and ischemia-related diseases and injuries. Additionally, this unexpected result indicates that there is a need in the art for further pharmaceutical compositions of chalcogenides, including those containing sulfide. Sulfide is defined as sulfur in its −2 valence state, either as $H_2S$ or as a salt thereof (e.g., NaHS, $Na_2S$, etc.) that may be conveniently administered to patients, in both a controlled medical environment, e.g., for treatment of disease or treatment in the field during an emergency, and in critical care in response to a catastrophic injury or life-threatening medical event. In addition to pharmaceutical compositions of known chalcogenides, there is a need in the art for further chalcogenide compounds and compositions comprising such compounds useful for treating or preventing injury of a biological material exposed to hypoxic or ischemic conditions.

Accordingly, while progress has been made in this field, there remains a need in the art for methods of treating or preventing injury of a biological material exposed to hypoxic or ischemic conditions as well as for chalcogenide compounds and pharmaceutical compositions useful for the same. The present invention fulfills this need and provides further related advantages.

BRIEF SUMMARY OF THE INVENTION

In brief, the present invention is directed to methods for treating or preventing injury of a biological material exposed to hypoxic or ischemic conditions comprising contacting the biological material with an effective amount of a compound of structure (I):

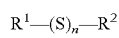

(I)

$R^1$—$(S)_n$—$R^2$ or a stereoisomer, pharmaceutically acceptable salt or prodrug thereof, wherein:

$R^1$ and $R^2$ are each independently selected from the group consisting of substituted or unsubstituted aryl, substituted or unsubstituted aralkyl, substituted or unsubstituted heteroaryl, and substituted or unsubstituted heteroarylalkyl; and n is an integer from 2-5.

In another embodiment, the present invention provides a compound having structure (IV):

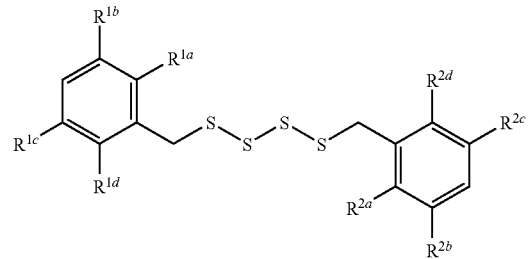

(IV)

or a stereoisomer, pharmaceutically acceptable salt or prodrug thereof, wherein:

$R^{1a}$, $R^{1b}$, $R^{1c}$, $R^{1d}$, $R^{2a}$, $R^{2b}$, $R^{2c}$, $R^{2d}$ are each independently selected from the group consisting of hydrogen, hydroxy, halogen, amino, substituted or unsubstituted $C_1$-$C_8$ alkyl, substituted or unsubstituted $C_1$-$C_8$ alkoxy, substituted or unsubstituted $C_1$-$C_8$ alkylamino, and —$CO_2Z$, wherein Z is hydrogen or substituted or unsubstituted $C_1$-$C_8$ alkyl, provided that:

(a) $R^{1a}$, $R^{1b}$, $R^{1c}$, $R^{1d}$, $R^{2a}$, $R^{2b}$, $R^{2c}$, and $R^{2d}$ are not all hydrogen;

(b) when $R^{1b}$, $R^{1c}$, $R^{2b}$ and $R^{2c}$ are all hydrogen, $R^{1a}$, $R^{1d}$, $R^{2a}$, and $R^{2d}$ are not all chloro; and (c) when $R^{1a}$, $R^{1b}$, $R^{1c}$, $R^{2a}$, $R^{2b}$, and $R^{2c}$ are all hydrogen, $R^{1d}$ and $R^{2d}$ are not both —$CO_2H$ or $R^{1d}$ and $R^{2d}$ are not both —$CO_2CH_3$.

In another embodiment, the present invention provides a compound having structure (V):

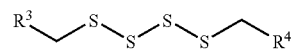

(V)

or a stereoisomer, pharmaceutically acceptable salt or prodrug thereof, wherein:

$R^3$ and $R^4$ are each independently selected from the group consisting of substituted or unsubstituted heteroaryl, provided that $R^3$ and $R^4$ are not both substituted or unsubstituted imidazolidine-2,4-dioneyl.

In another embodiment, the present invention provides a pharmaceutical composition comprising a pharmaceutically acceptable carrier or diluent in combination with a compound of structure (II).

In another embodiment, the present invention provides a pharmaceutical composition comprising a pharmaceutically acceptable carrier or diluent in combination with a compound of structure (III).

These and other aspects of the invention will be apparent upon reference to the following detailed description.

DETAILED DESCRIPTION OF THE INVENTION

Figure 1:
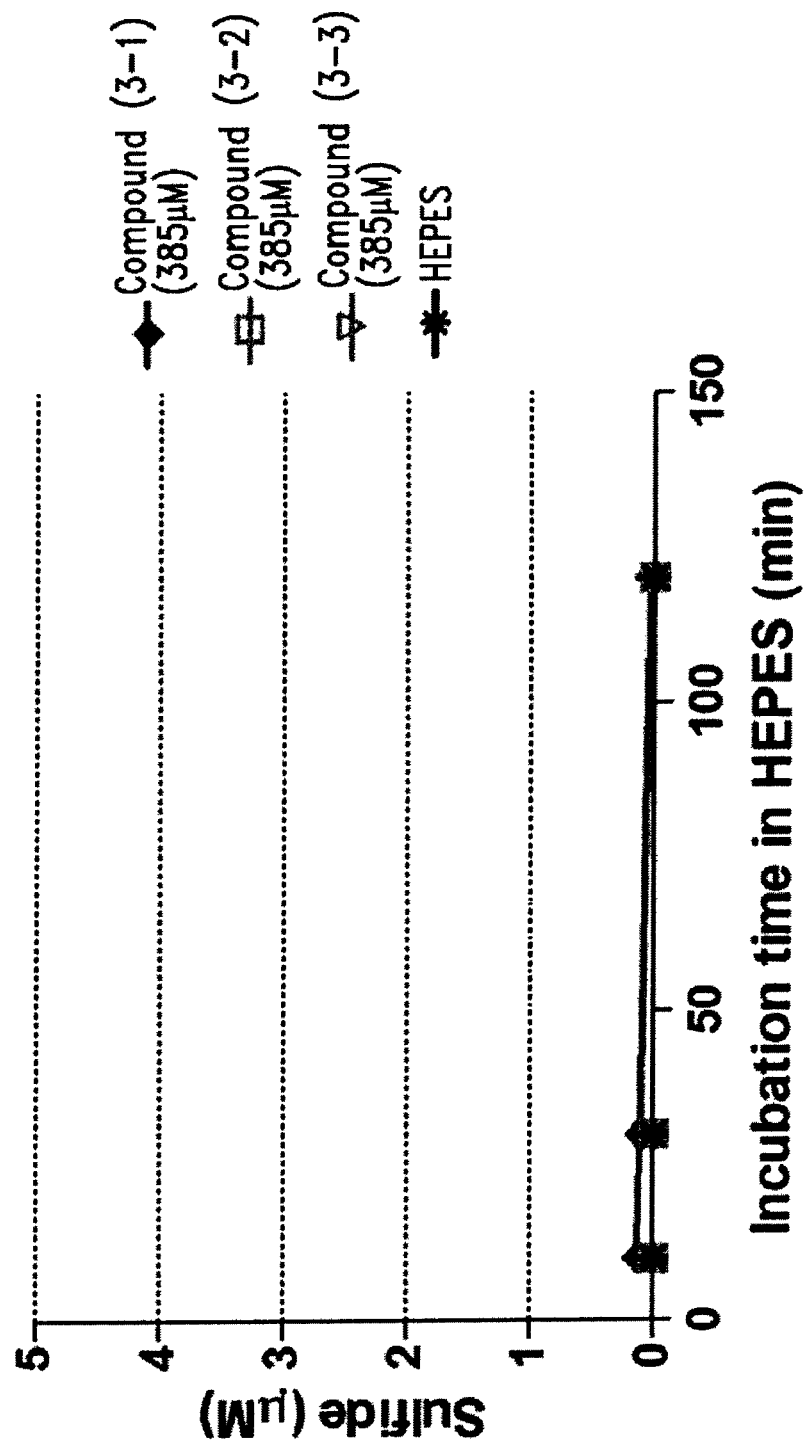
FIG. 1 shows analysis of sulfide release from polysulfide compounds in HEPES buffer via monobromobimane derivatization.

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Reference throughout this specification to "compounds of the present invention" or "compound of the invention" means a compound of structure (I), (II), or (III), and all embodiments thereof.

"Amino" refers to the —$NH_2$ radical.

"Cyano" refers to the —CN radical.

"Hydroxy" or "hydroxyl" refers to the —OH radical.

"Imino" refers to the =NH substituent.

"Nitro" refers to the —$NO_2$ radical.

"Oxo" refers to the =O substituent.

"Thioxo" refers to the =S substituent.

"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Alkoxy" refers to a radical of the formula —$OR_a$ where $R_a$ is an alkyl radical as defined above containing one to twelve carbon atoms. Unless stated otherwise specifically in the specification, an alkoxy group may be optionally substituted.

"Alkylamino" refers to a radical of the formula —$NHR_a$ or —$NR_aR_a$ where each $R_a$ is, independently, an alkyl radical as defined above containing one to twelve carbon atoms. Unless stated otherwise specifically in the specification, an alkylamino group may be optionally substituted.

"Thioalkyl" refers to a radical of the formula —$SR_a$ where $R_a$ is an alkyl radical as defined above containing one to twelve carbon atoms. Unless stated otherwise specifically in the specification, a thioalkyl group may be optionally substituted.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, //as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$-$R_c$ where $R_b$ is an alkylene chain as defined above and $R_c$ is one or more aryl radicals as defined above, for example, benzyl, diphenylmethyl and the like. Unless stated otherwise specifically in the specification, an aralkyl group may be optionally substituted.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted.

"Cycloalkylalkyl" refers to a radical of the formula —$R_bR_d$ where $R_b$ is an alkylene chain as defined above and $R_d$ is a cycloalkyl radical as defined above. Unless stated otherwise specifically in the specification, a cycloalkylalkyl group may be optionally substituted.

"Cycloalkylamino" refers to a radical of the formula —$NHR_g$ or —$NR_gR_g$ where each $R_g$ is, independently, a cycloalkyl radical as defined above. Unless stated otherwise specifically in the specification, a cycloalkylamino group may be optionally substituted.

"Oxycarbonyl" refers to a radical of the formula —OC(=O)$R_i$ where $R_i$ is an alkyl radical or aryl radical as defined above.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, Unless stated otherwise specifically in the specification, a heterocyclyl group may be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group may be optionally substituted.

"Heterocyclylalkyl" refers to a radical of the formula —$R_bR_e$ where $R_b$ is an alkylene chain as defined above and $R_e$ is a heterocyclyl radical as defined above, and if the heterocyclyl is a nitrogen-containing heterocyclyl, the heterocyclyl may be attached to the alkyl radical at the nitrogen atom. Unless stated otherwise specifically in the specification, a heterocyclylalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula —$R_bR_f$ where $R_b$ is an alkylene chain as defined above and $R_f$ is a heteroaryl radical as defined above. Unless stated otherwise specifically in the specification, a heteroarylalkyl group may be optionally substituted.

"Polysulfide" refers to a chain of sulfur atoms linked by sulfur-sulfur bonds. A polysulfide may be linear, branched or cyclic and is composed of n sulfur atoms, wherein n is defined herein. Examples of polysulfide radicals include, but are not limited to disulfide (n=2, i.e., —S—S—), trisulfide (n=3, i.e., —S—S—S—), and tetrasulfide (n=4, i.e., —S—S—S—S—), etc. A polysulfide compound contains one or more polysulfides.

The term "substituted" used herein means any of the above groups (i.e., alkyl, alkylene, alkoxy, alkylamino, thioalkyl, aryl, aralkyl, cycloalkyl, cycloalkylalkyl, cycloalkylamino, oxycarbonyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, cyclo alkyl amino, oxycarbonyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

"Prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like.

The invention disclosed herein is also meant to encompass all pharmaceutically acceptable compounds of structures (I), (II), and (III) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{123}I$, respectively. These radiolabelled compounds could be useful to help determine or measure the effectiveness of the compounds, by characterizing, for example, the site or mode of action, or binding affinity to pharmacologically important site of action. Certain isotopically-labelled compounds of structures (I), (II), and (III) for example, those incorporating a radioactive isotope, are useful in drug and/or substrate tissue distribution studies. The radioactive isotopes tritium, i.e., $^3H$, and carbon-14, i.e., $^{14}C$, are particularly useful for this purpose in view of their ease of incorporation and ready means of detection.

"Stable compound" and "stable structure" are meant to indicate a compound that is sufficiently robust to survive isolation to a useful degree of purity from a reaction mixture, and formulation into an efficacious therapeutic agent. "Biological material" and "biological matter" includes cells, tissues, organs, organisms and animals (including, mammals). It is contemplated that the methods of the present invention may be practiced on a part of an organism (such as in cells, in tissue, and/or in one or more organs), whether that part remains within the organism or is removed from the organism, or on the whole organism.

"Cell" includes, but is not limited to, mammalian cells. Mammalian cells include, but are not limited to those from a human, monkey, mouse, rat, rabbit, hamster, goat, pig, dog, cat, ferret, cow, sheep, or horse. Moreover, cells of the invention may be diploid, but, in some cases, the cells are haploid (sex cells). Additionally, cells may be polyploid, aneuploid, or anucleate. The cell can be from a particular tissue or organ, such as heart, lung, kidney, liver, bone marrow, pancreas, skin, bone, vein, artery, cornea, blood, small intestine, large intestine, brain, spinal cord, smooth muscle, skeletal muscle, ovary, testis, uterus, and umbilical cord. In certain embodiments, the cell can be characterized as one of the following cell types: platelet, myelocyte, erythrocyte, lymphocyte, adipocyte, fibroblast, epithelial cell, endothelial cell, smooth muscle cell, skeletal muscle cell, endocrine cell, glial cell, neuron, secretory cell, barrier function cell, contractile cell, absorptive cell, mucosal cell, limbus cell (from cornea), stem cell (totipotent, pluripotent or multipotent), unfertilized or fertilized oocyte, or sperm.

"Tissue" and "organ" are used according to their ordinary and plain meanings. Though tissue is composed of cells, it will be understood that the term "tissue" refers to an aggregate of similar cells forming a definite kind of structural material. Moreover, an organ is a particular type of tissue. In certain embodiments, the tissue or organ is "isolated," meaning that it is not located within an organism.

"Mammal" includes humans and both domestic mammals such as laboratory animals and household pets (e.g., cats, dogs, swine, cattle, sheep, goats, horses, rabbits), and non-domestic mammals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Effective amount" or "therapeutically effective amount" refers to that amount of a compound of the invention which, when administered to a biological material, such as, a mammal, is sufficient to effect treatment, as defined below, of treating or preventing injury of a biological material exposed to hypoxic or ischemic conditions. The amount of a compound of the invention which constitutes a "therapeutically effective amount" will vary depending on the compound, the condition and its severity, the manner of administration, and the biological material (e.g., the age of the mammal to be treated), but can be determined routinely by one of ordinary skill in the art having regard to his own knowledge and to this disclosure. For example, in one embodiment, the term "effective amount" refers to the amount that can achieve a measurable result. In one embodiment, an "effective amount" is, for example, an amount that when administered to a human subject in need of medical treatment in a controlled Phase 2 or Phase 3 clinical trial produces a statistically significant benefit on a predefined clinical endpoint (e.g., mortality). An effective amount enhances the survivability of biological matter in response to a disease or injury, or an amount that induces stasis or pre-stasis in the biological matter.

"Treating" or "treatment" as used herein covers the treatment of the disease or condition of interest in a biological material (e.g., a mammal) having the disease or condition of interest, and includes, for example:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The terms "hypoxia" and "hypoxic" refer to an environment with levels of oxygen below normal. Hypoxia occurs when the normal physiologic levels of oxygen are not supplied to a cell, tissue, or organ. "Normoxia" refers to normal physiologic levels of oxygen for the particular cell type, cell state or tissue in question. "Anoxia" is the absence of oxygen. "Hypoxic conditions" are those leading to cellular, organ or organismal hypoxia. For purposes of the present invention, hypoxic conditions include conditions in which oxygen concentration is at or less than normal atmospheric conditions, that is less that 20.8, 20, 19, 18, 17, 16, 15, 14, 13, 12, 11, 10, 9, 8, 7, 6, 5, 4, 3, 2, 1, 0.5, 0%. Alternatively, these numbers could represent the percent of atmosphere at 1 atmosphere of pressure (101.3 kPa). "Anoxia" is the absence of oxygen.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "complexing agent" is a molecule, typically an organic molecule, which binds a metal ion through two or more of the complexing agent's atoms.

A "co-solvent" is any solvent or compound present in a mixture in addition to the primary solvent. Co-solvents are typically added to increase or decrease the solubility of the solutes.

The chemical naming protocol and structure diagrams used herein are a modified form of the I.U.P.A.C. nomenclature system, using the ACD/Name Version 9.07 software program and/or ChemDraw Ultra Version 11.0 software naming program (CambridgeSoft).

As noted above, in one embodiment of the present invention, a method for treating or preventing injury of a biological material exposed to hypoxic or ischemic conditions is provided, wherein the method comprises contacting the biological material with an effective amount of a compound of structure (I):

$$R^1-(S)_n-R^2 \qquad (I)$$

or a stereoisomer, pharmaceutically acceptable salt or prodrug thereof, wherein:

$R^1$ and $R^2$ are each independently selected from the group consisting of substituted or unsubstituted aryl, substituted or unsubstituted aralkyl, substituted or unsubstituted heteroaryl, and substituted or unsubstituted heteroarylalkyl; and n is an integer from 2-5.

In further embodiments, n is 2, 3, or 5. In other further embodiments, n is 4.

In other further embodiments, $R^1$ and $R^2$ are each substituted or unsubstituted aryl. In certain embodiments, $R^1$ and $R^2$ are each substituted or unsubstituted phenyl. In certain embodiments, the compound has the following structure (II):

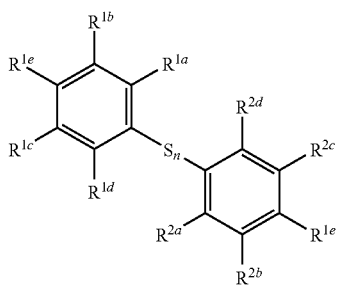

(II)

or a stereoisomer, pharmaceutically acceptable salt or prodrug thereof, wherein:

n is 2, 3, 4 or 5; and $R^{1a}$, $R^{1b}$, $R^{1c}$, $R^{1d}$, $R^{1e}$, $R^{2a}$, $R^{2b}$, $R^{2c}$, $R^{2d}$, and $R^{2e}$ are each independently selected from the group consisting of hydrogen, hydroxy, halogen, amino, substituted or unsubstituted $C_1$-$C_8$ alkyl, substituted or unsubstituted $C_1$-$C_8$ alkoxy, substituted or unsubstituted $C_1$-$C_8$ alkylamino, and —$CO_2Z$, wherein Z is hydrogen or substituted or unsubstituted $C_1$-$C_8$ alkyl.

In more specific embodiments of the foregoing, n is 2, 3 or 5. In certain embodiments, the compound has one of the following structures:

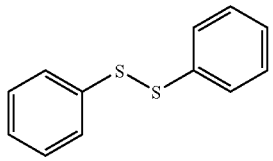

(1-1)

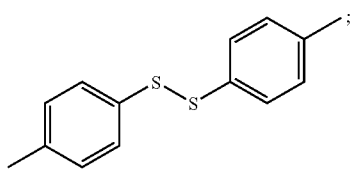

(1-10)

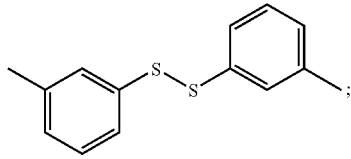

(1-11)

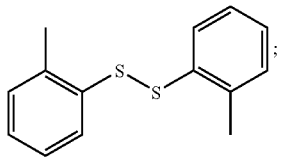

(1-12)

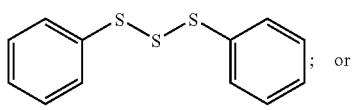

(2-2)

; or

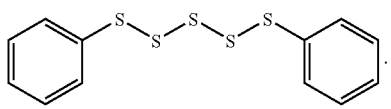

(4-2)

In other more specific embodiments of the foregoing, n is 4. In certain embodiments, the compound has one of the following structures:

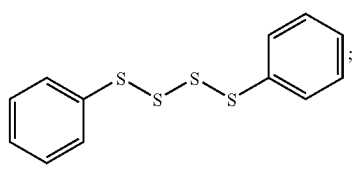

(3-8)

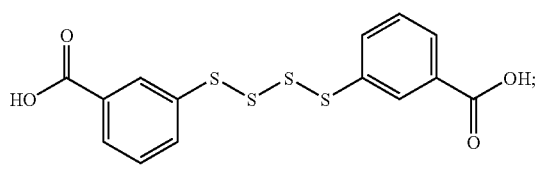

(3-15)

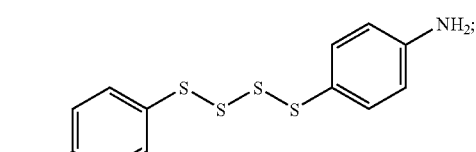

(3-16)

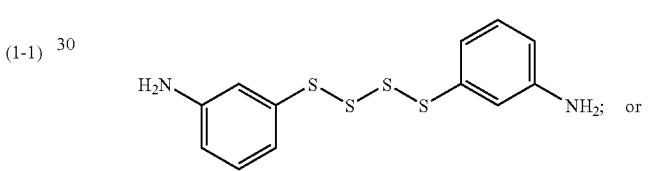

(3-26)

; or

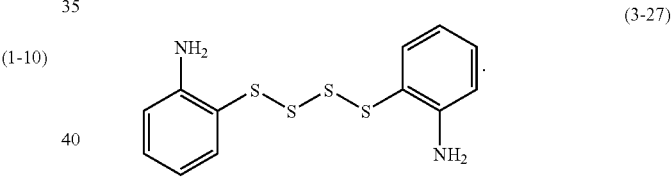

(3-27)

In other further embodiments, $R^1$ and $R^2$ are each substituted or unsubstituted aralkyl. In certain embodiments, $R^1$ and $R^2$ are each substituted or unsubstituted benzyl. In certain embodiments, the compound has the following structure (III):

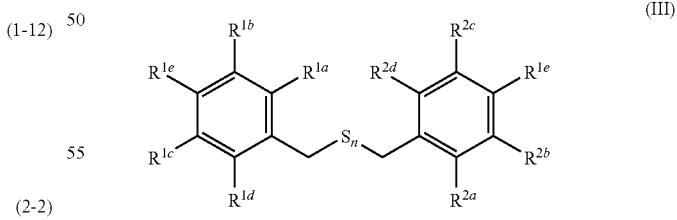

(III)

or a stereoisomer, pharmaceutically acceptable salt or prodrug thereof, wherein:

n is 2, 3, 4 or 5; and $R^{1a}$, $R^{1b}$, $R^{1c}$, $R^{1d}$, $R^{1e}$, $R^{2a}$, $R^{2b}$, $R^{2c}$, $R^{2d}$, and $R^{2e}$ are each independently selected from the group consisting of hydrogen, hydroxy, halogen, amino, substituted or unsubstituted $C_1$-$C_8$ alkyl, substituted or unsubstituted $C_1$-$C_8$ alkoxy, substituted or unsubstituted $C_1$-$C_8$ alkylamino, and —$CO_2Z$, wherein Z is hydrogen or substituted or unsubstituted $C_1$-$C_8$ alkyl.

In more specific embodiments of the foregoing, n is 2, 3 or 5. In certain embodiments, the compound has one of the following structures:

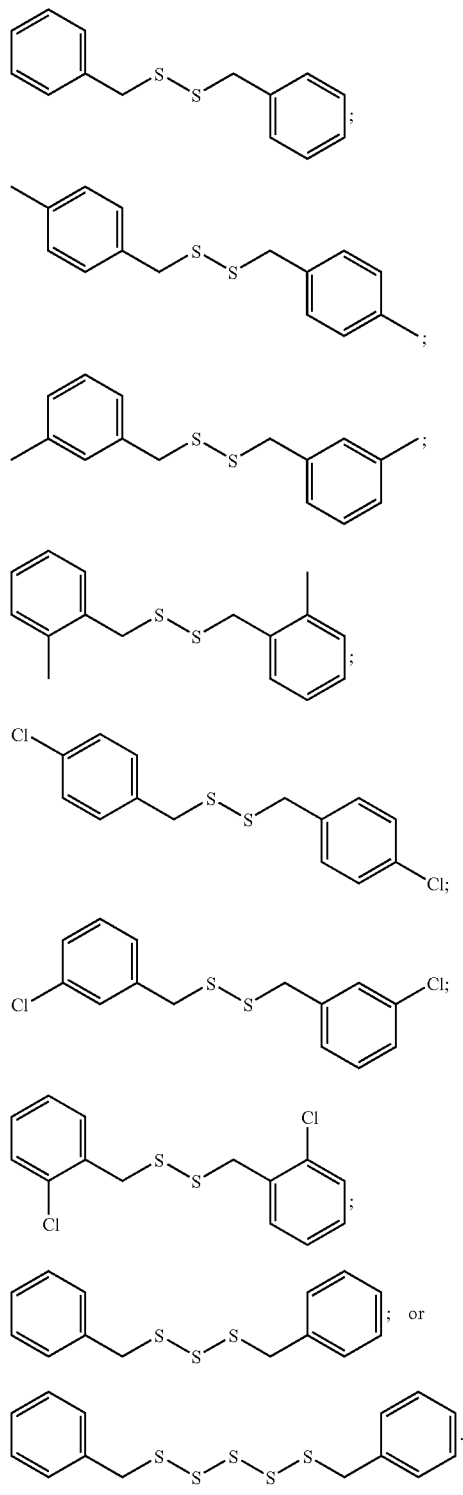

In other more specific embodiments of the foregoing, n is 4. In certain embodiments, the compound has one of the following structures:

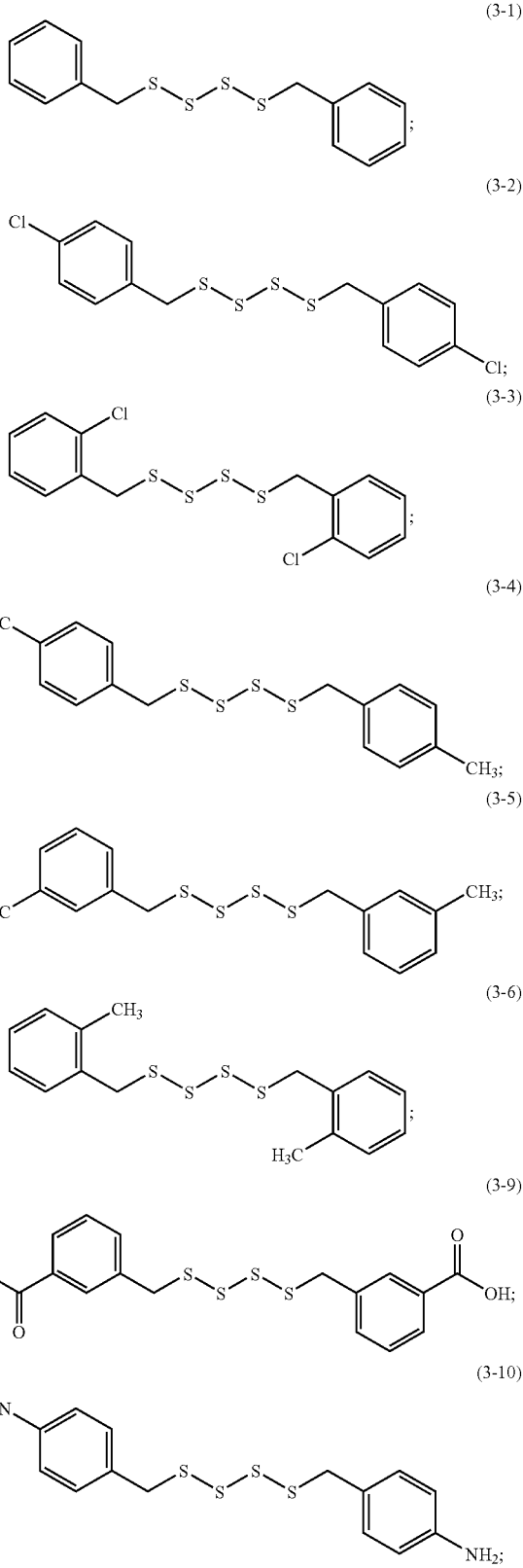

-continued

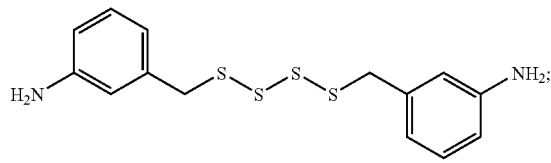
(3-24)

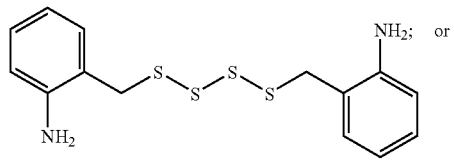
(3-25)

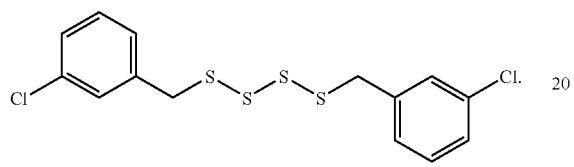
(3-23)

In other further embodiments, $R^1$ and $R^2$ are each substituted or unsubstituted heteroaryl. In certain embodiments, the compound has one of the following structures:

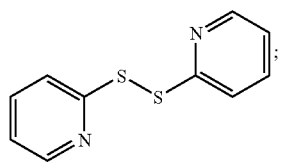
(1-13)

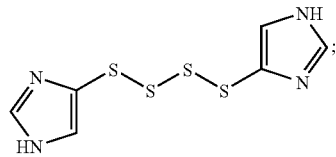
(3-17)

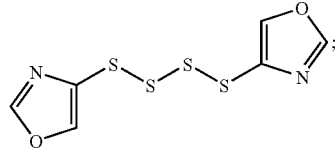
(3-18)

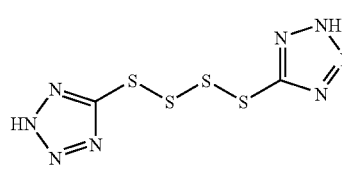
(3-19)

(3-20)

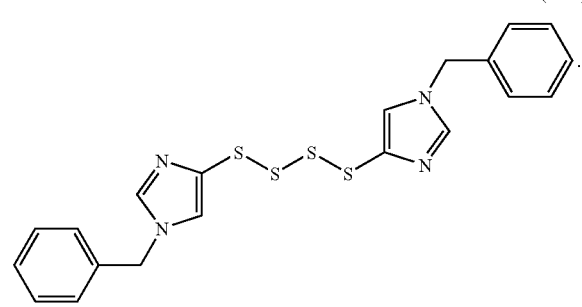

In other further embodiments, $R^1$ and $R^2$ are each substituted or unsubstituted heteroarylalkyl. In certain embodiments, the compound has one of the following structures:

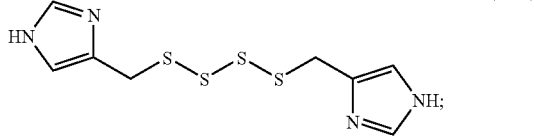
(3-11)

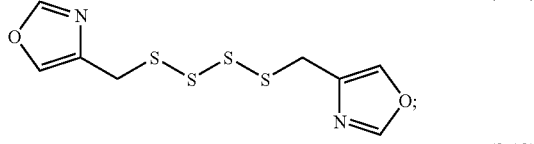
(3-12)

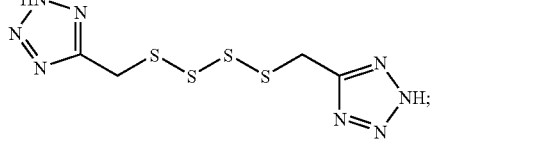
(3-13)

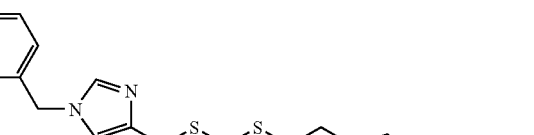
(3-14)

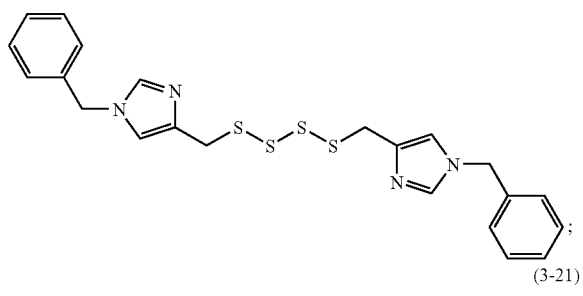

(3-21)

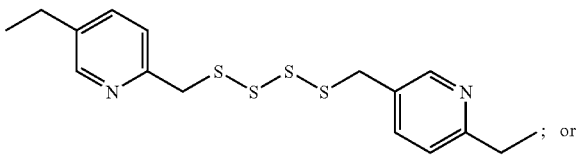

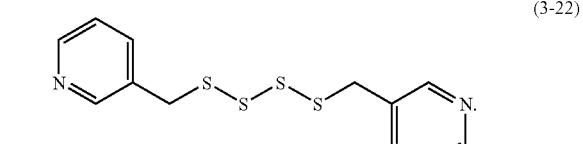
(3-22)

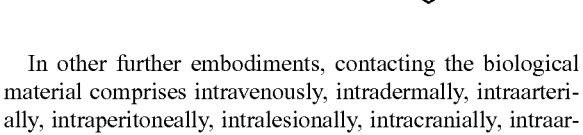

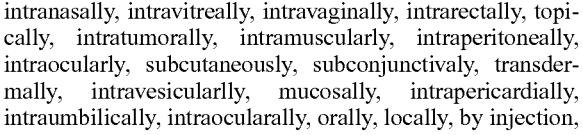

In other further embodiments, contacting the biological material comprises intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, intraocularly, subcutaneously, subconjunctivaly, transdermally, intravesicularlly, mucosally, intrapericardially, intraumbilically, intraocularally, orally, locally, by injection, by infusion, by continuous infusion, by absorption, by adsorption, by immersion, by localized perfusion, via a catheter, or via a lavage.

In other further embodiments, the hypoxic or ischemic condition results from an injury to the biological material, the onset or progression of a disease that adversely affects the biological material, or hemorrhaging of the biological material. In certain embodiments, the biological material is contacted with the compound before the injury, before the onset or progression of the disease, or before hemorrhaging of the biological material. In certain embodiments, the injury is from an external physical force (such as, a surgery). In certain embodiments, the biological material is contacted with the compound in an amount and for a time that protects the biological material from damage or death resulting from the injury, the onset or progression of the disease, or hemorrhaging in the biological material.

In other further embodiments, the biological material is selected from the group consisting of cells, tissues, organs, organisms, and animals. For example, in certain embodiments, the biological material is an animal. In certain embodiments, the animal is a mammal. In certain embodiments, the mammal is a human. In other embodiments, the biological material comprises platelets. In other embodiments, the biological material is to be transplanted. In other embodiments, the biological material is at risk for reperfusion injury. In other embodiments, the biological material is at risk for hemorrhagic shock.

In other further embodiments, the hypoxic or ischemic conditions result in myocardial infarction, sepsis, vascular abnormalities, cirrhosis, vascular calcification, gastric injury induced by drug treatment, burns, lung injury, neutrophil adhesion, leukocyte-mediated inflammation, erectile dysfunction, irritable bowel syndrome, anti-nociceptive effects in post-inflammatory hypersensitivity, acute coronary syndrome, cardiac arrest, planned cardiac bypass surgery, congestive heart failure, neonatal hypoxia/ischemia, myocardial ischemic reperfusion injury, unstable angina, post-angioplasty, aneurysm, trauma, stroke, hemorrhagic shock, and/or blood loss.

In another embodiment of the present invention, a compound is provided, wherein the compound has the following structure (IV):

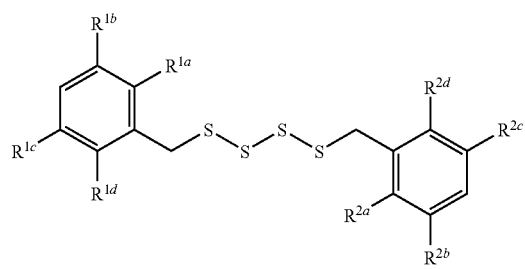

(IV)

or a stereoisomer, pharmaceutically acceptable salt or prodrug thereof,
wherein:
$R^{1a}$, $R^{1b}$, $R^{1c}$, $R^{1d}$, $R^{2a}$, $R^{2b}$, $R^{2c}$, and $R^{2d}$ are each independently selected from the group consisting of hydrogen, hydroxy, halogen, amino, substituted or unsubstituted $C_1$-$C_8$ alkyl, substituted or unsubstituted $C_1$-$C_8$ alkoxy, substituted or unsubstituted $C_1$-$C_8$ alkylamino, and —$CO_2Z$, wherein Z is hydrogen or substituted or unsubstituted $C_1$-$C_8$ alkyl, provided that:
(a) $R^{1a}$, $R^{1b}$, $R^{1c}$, $R^{1d}$, $R^{2a}$, $R^{2b}$, $R^{2c}$, and $R^{2d}$ are not all hydrogen;
(b) when $R^{1b}$, $R^{1c}$, $R^{2b}$ and $R^{2c}$ are all hydrogen, $R^{1a}$, $R^{1d}$, $R^{2a}$, and $R^{2d}$ are not all chloro; and
(c) when $R^{1a}$, $R^{1b}$, $R^{1c}$, $R^{2a}$, $R^{2b}$, and $R^{2c}$ are all hydrogen, $R^{1d}$ and $R^{2d}$ are not both —$CO_2H$ or —$CO_2CH_3$.

In further embodiments of the foregoing, the compound has one of the following structures:

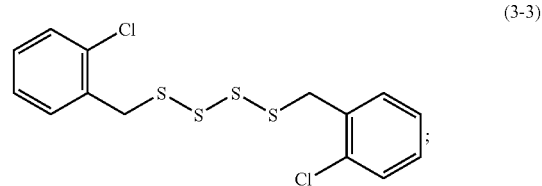

(3-3)

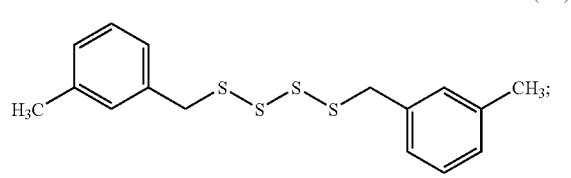

(3-5)

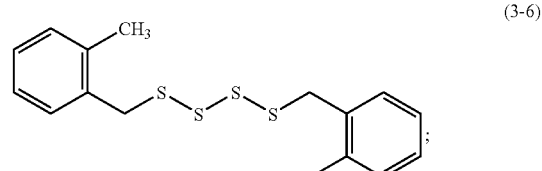

(3-6)

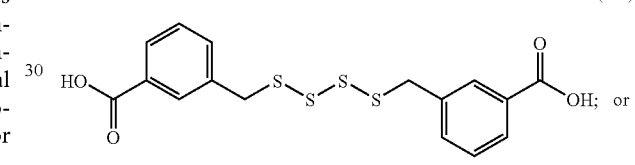

(3-9)

or

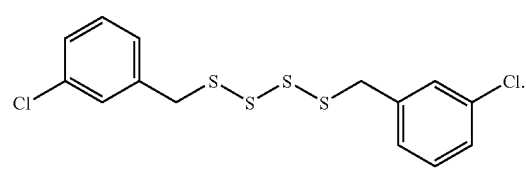

(3-23)

In another embodiment of the present invention, a compound is provided, wherein the compound has the following structure (V):

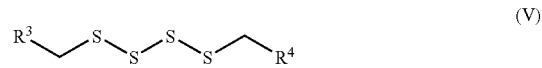

(V)

or a stereoisomer, pharmaceutically acceptable salt or prodrug thereof,
wherein:
$R^3$ and $R^4$ are each independently selected from the group consisting of substituted or unsubstituted heteroaryl, provided that $R^3$ and $R^4$ are not both substituted or unsubstituted imidazolidine-2,4-dioneyl.

In further embodiments of the foregoing, $R^3$ and $R^4$ are each independently selected from the group consisting of substituted or unsubstituted imidazolyl, substituted or unsubstituted oxazolyl, substituted or unsubstituted tetrazolyl and substituted or unsubstituted pyridinyl. For example, in some embodiments, the compound has one of the following structures:

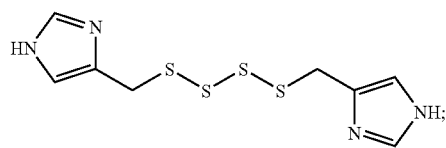
(3-11)

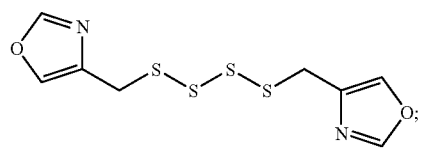
(3-12)

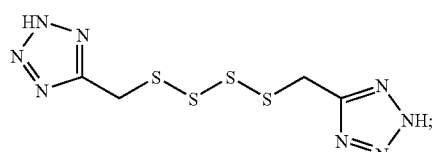
(3-13)

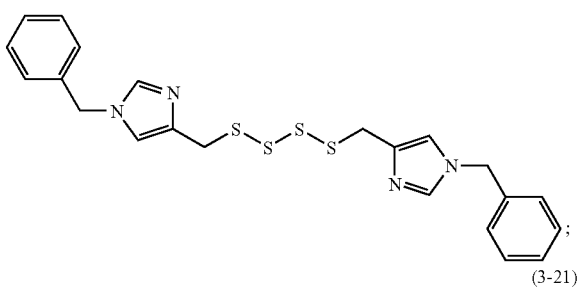
(3-14)

(3-21)

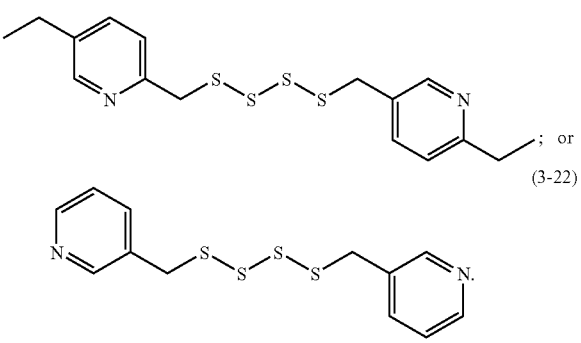
; or (3-22)

In another embodiment of the present invention, a pharmaceutical composition is provided, wherein the pharmaceutical composition comprises a pharmaceutically acceptable carrier or diluent in combination with a compound of structure (IV).

In another embodiment of the present invention, a pharmaceutical composition is provided, wherein the pharmaceutical composition comprises a pharmaceutically acceptable carrier or diluent in combination with a compound of structure (V).

In further embodiments of the foregoing, the pharmaceutical composition comprising a compound of structure (IV) or structure (V) further comprises one or more surfactant, one or more complexing agent, and/or one or more co-solvent.

It is understood that any embodiment of the compounds of structures (I), (II), (III), (IV) or (V), as set forth above, and any specific substituent set forth herein for a $R^1$, $R^2$, $R^{1a}$, $R^{1b}$, $R^{1c}$, $R^{1d}$, $R^{2a}$, $R^{2b}$, $R^{2c}$, $R^{2d}$, $R^3$ or $R^4$ group in the compounds of structures (I), (II), (III), (IV) or (V), as set forth above, may be independently combined with other embodiments and/or substituents of compounds of structures (I), (II), (III), (IV) or (V) to form embodiments of the inventions not specifically set forth above. In addition, in the event that a list of substituents is listed for any particular $R^1$, $R^2$, $R^{1a}$, $R^{1b}$, $R^{1c}$, $R^{1d}$, $R^{1e}$, $R^{2a}$, $R^{2b}$, $R^{2c}$, $R^{2d}$, $R^{2e}$, $R^3$ or $R^4$ group in a particular embodiment and/or claim, it is understood that each individual substituent may be deleted from the particular embodiment and/or claim and that the remaining list of substituents will be considered to be within the scope of the invention.

It is understood that in the present description, combinations of substituents and/or variables of the depicted formulae are permissible only if such contributions result in stable compounds.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

For the purposes of administration, the compounds of the present invention may be administered as a raw chemical or may be formulated as pharmaceutical compositions. Pharmaceutical compositions of the present invention comprise a compound of structures (I), (II), (III), (IV) or (V) and a pharmaceutically acceptable carrier, diluent or excipient. The compound of structures (I), (II), (III), (IV) or (V) is present in the composition in an amount which is effective to treat a particular disease or condition of interest—that is, in an amount sufficient to treat or prevent injury of a biological material exposed to hypoxic or ischemic conditions, and preferably with acceptable toxicity. Sulfide releasing activity of compounds of structures (I), (II), (III), (IV) or (V) can be determined by one skilled in the art, for example, as described in the Examples below. Appropriate concentrations and dosages can be readily determined by one skilled in the art.

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient.

Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see, *Remington: The Science and Practice of Pharmacy,* 21st Edition (Philadelphia College of Pharmacy and Science, 2005). The composition to be administered will, in any event, contain a therapeutically effective amount of a compound of the invention, or a pharmaceutically acceptable salt thereof, for treatment of a disease or condition of interest in accordance with the teachings of this invention.

The compounds of the present invention may be used to treat or prevent a variety of diseases and disorders, including any disease or disorder that has been treated using a chalcogenide (see U.S. Patent Application Publication No. 2008/0199541) or a chalcogenide composition. For example, treatment with sodium sulfide has been used in an animal model as a potential treatment for myocardial infarction, sepsis (see Hui, et al. J Infect (2003):47:155), congestive heart failure, vascular abnormalities in cirrhosis (see Fiorucci S, et al., Hepatology. (2005) 42:539), as a cardioprotectant (see Geng, et al., Biochem and Biophy Res Com (2004) 313:362), as a neuroprotectant (see Qu K. et al, *Stroke.* (2006) 889), in myocardial ischemia reperfusion injury (see Johansen et al., Basic Res Cardiol (2006) 101: 53), to reduce vascular calcification (see Wu et al., Acta Pharmacol Sin. (2006) 27:299), to reduce gastric injury induced by drug treatment (see Fiorucci, S. et al., *Gastroenterology* (2005) 129:1210), to reduce neutrophil adhesion and to modulate leukocyte-mediated inflammation (see Zanardo et al., FASEB J. (2006) 20: 2118-2120), in erectile dysfunction (see Srilatha B. et al., *Eur J Pharmacol.* (2006) 535:280), irritable bowel syndrome (see Distrutti E., et al., JPET (2006) 319:447) and for anti-nociceptive effects in post-inflammatory hypersensitivity.

As noted above, the compounds of the present invention may be used to treat or prevent injury of a biological matter exposed to ischemic or hypoxic conditions. In one embodiment, these methods are used to treat patients who have undergone, are undergoing, or who are susceptible to injury, trauma or critical care treatment. Injury may be caused by external insults, such as burns, wounds, amputations, gunshot wounds, or surgical trauma, abdominal surgery, prostate surgery, internal insults, such as septic shock, stroke or cardiac arrest, heart attack that result in the acute reduction in circulation, or reductions in circulation due to non-invasive stress, such as exposure to cold or radiation. On a cellular level, injury often results in exposure of cells, tissues and/or organs to hypoxia, thereby resulting in induction of programmed cell death, or "apoptosis."

Therefore, the present invention contemplates contacting tissues, organs, limbs and even whole organisms with an effective amount of a compound of the present invention as a way of protecting them from the detrimental effects of injury. In a specific scenario, where medical attention is not readily available, this can "buy time" for a patient, until they can receive appropriate medical attention. The present invention also contemplates methods for inducing tissue regeneration and wound healing by prevention/delay of biological processes that may result in delayed wound healing and tissue regeneration. In this context, in scenarios in which there is a substantial wound to the limb or organism, contacting the biological matter with a compound of the present invention aids in the wound healing and tissue regeneration process by managing the biological processes that inhibit healing and regeneration. In addition to wound healing, methods of the invention can be implemented to prevent or treat trauma such as cardiac arrest or stroke, and hemorrhagic shock. The invention has importance with respect to the risk of trauma from emergency surgical procedures, such as thoracotomy, laparotomy, and splenic transaction or cardiac surgery, aneurysm, surgery, brain surgery and the like.

In certain embodiments, methods of the present invention can be implemented to enhance survivability and prevent ischemic injury resulting from cardiac arrest or stroke. Accordingly, in one embodiment, the present invention includes methods of enhancing survivability or reducing ischemic injury in a patient suffering from or at risk of cardiac arrest or stroke, comprising providing an effective amount of a compound of the present invention to the patient before, after, or both before and after myocardial infarction, cardiac arrest or stroke.

In certain embodiments, methods of the present invention include pre-treating a biological material, e.g., a patient, prior to an ischemic or hypoxic injury or disease insult. These methods can be used when an injury or disease with the potential to cause ischemia or hypoxia is scheduled or elected in advance, or predicted in advance to likely occur. Examples include, but are not limited to, major surgery where blood loss may occur spontaneously or as a result of a procedure, cardiopulmonary bypass in which oxygenation of the blood may be compromised or in which vascular delivery of blood may be reduced (as in the setting of coronary artery bypass graft (CABG) surgery), or in the treatment of organ donors prior to removal of donor organs for transport and transplantation into a recipient in need of an organ transplant. Examples include, but are not limited to, medical conditions in which a risk of injury or disease progression is inherent (e.g., in the context of unstable angina, following angioplasty, bleeding aneurysms, hemorrhagic strokes, following major trauma or blood loss, congestive heart failure), or in which the risk can be diagnosed using a medical diagnostic test.

Moreover, additional embodiments of the invention concern enhancing survivability and preventing irreversible tissue damage from blood loss or other lack of oxygenation to cells or tissue, such as from lack of an adequate blood supply. This may be the result of, for example, actual blood loss, or it may be from conditions or diseases that cause blockage of blood flow to cells or tissue, that reduce blood pressure locally or overall in an organism, that reduce the amount of oxygen that is carried in the blood, or that reduces the number of oxygen carrying cells in the blood. Conditions and diseases that may be involved include, but are not limited to, blood clots and embolisms, cysts, growths, tumors, anemia (including sickle cell anemia), hemophilia, other blood clotting diseases (e.g., von Willebrand, or ITP), and atherosclerosis. Such conditions and diseases also include those that create essentially hypoxic or anoxic conditions for cells or tissue in an organism because of an injury, disease, or condition.

In one embodiment, the present invention provides methods to enhance the survivability of and prevent injury or damage to biological material undergoing hemorrhagic shock, which include contacting the biological material at risk of or in a state of hemorrhagic shock with an effective amount of a compound of the present invention as soon as practical, ideally within one hour of the injury. This method allows for the patient to be transported to a controlled environment (e.g., surgery), where the initial cause of the injury can be addressed, and then the patient can be brought back to normal function in a controlled manner. For this indication, the first hour after injury, referred to as the "golden hour," is crucial to a successful outcome.

In various other embodiments, the methods of the present invention may be used in the treatment of neurodegenerative diseases associated with ischemia or hypoxia, in the treatment of hypothermia, in the treatment of hyperproliferative disorders, and in the treatment of immune disorders. In various other embodiments, the biological condition is any one or combination of the following: neurological disease, cardiovascular disease, metabolic disease, infectious disease, lung disease, genetic disease, autoimmune disease, and immune-related disease.

In certain embodiments, the methods of the present invention are used to enhance the survivability of ex vivo biological matter subjected to hypoxic or ischemic conditions, including, e.g., isolated cells, tissues and organs. Specific examples of such ex vivo biological material include platelets and other blood products, as well as tissues and organs to be transplanted.

In one embodiment, methods of the present invention may be used to enhance survivability of biological material in the laboratory or research context, for example when cell lines or laboratory organisms are purposefully subjected to hypoxic or ischemic conditions, e.g., during cryopreservation and storage. For example, cells, tissues or organs may be stored or transported in the presence of a compound of the present invention. The methods of the present invention may be used to increase the survivability of donor tissues and organs, thereby extending the time before the donor tissue must be transplanted into a recipient and blood flow restored. These methods may be combined with current preservation methods, including the use of other preservation agents and oxygen perfusion. The present invention provides methods of enhancing survivability of platelets, including, in particular embodiments, platelets stored in an anoxic environment, comprising contacting the platelets with an effective amount of a compound of the present invention during storage.

The present invention also provides methods and compositions for preserving both non-living biological material and preserving or extending the shelf-life of non-biological material. These methods comprise contacting the non-living biological matter or non-biological material with a compound of the present invention. In certain embodiments, the amount of a compound of the present invention that is provided to a biological material is about, at least, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 mg, mg/kg, or mg/m2, or any range derivable therein. Alternatively, the amount may be expressed as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 mM or M, or any range derivable therein.

In various embodiments of the present invention, a biological material is exposed to a compound of the present invention for about, at least, at least about, or at most about 30 seconds, 1, 2, 3, 4, 5, 10, 15, 20, 25, 30, 35, 40, 45, 50, 55 minutes, 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7 days or more, and any range or combination therein.

Furthermore, when administration is intravenous, it is contemplated that the following parameters may be applied. A flow rate of about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 gtts/min or µgtts/min, or any range derivable therein. In some embodiments, the amount of the solution is specified by volume, depending on the concentration of the compound of the present invention. An amount of time may be about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 minutes, 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7 days, 1, 2, 3, 4, 5 weeks, and/or 1, 2, 3, 4, 5, 6, 7, 8, 9, 10, 11, 12 months, or any range derivable therein.

Volumes of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 mls or liters, or any range therein, may be administered overall or in a single session.

The following Reaction Schemes illustrate methods of making representative compounds of the present invention, e.g., compounds of structure (I):

$$R^1-(S)_n-R^2 \quad (I)$$

wherein $R^1$, $R^2$, and n are as defined above. It is understood that one skilled in the art may be able to make these compounds by similar methods or by combining other methods known to one skilled in the art. It is also understood that one skilled in the art would be able to make, in a similar manner as described below, other compounds of structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Advanced Organic Chemistry:

Reactions, Mechanisms, and Structure, 5th edition (Wiley, December 2000)) or prepared as described in this invention.

Reaction Scheme 1

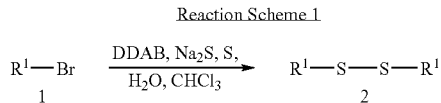

As shown in Reaction Scheme 2, compounds of structure (I) wherein n is 2 (compound 2) can be prepared by a modification of the procedure described by Sonavane et al. (Tetrahedron Letters 2007, 48 (34), 6048-6050). Referring to Reaction Scheme 1, wherein R' is as defined herein, compounds of structure 1 can be purchased or prepared according to methods known to those skilled in the art (for an example, see Reaction Scheme 3 below) and reacted with sulfur powder, sodium sulfide and didecyldimethyl-ammonium bromide (DDAB) in an appropriate solvent to yield disulfides of structure 2.

Reaction Scheme 2

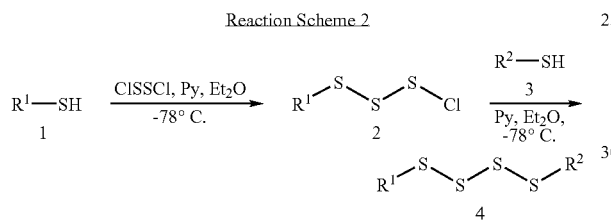

As shown in Reaction Scheme 2, compounds of structure (I) wherein n is 3 (compound 2) and n is 4 (compound 4) can be prepared by a modification of the procedure described by Derbesy et al. (Tetrahedron Letters 1994, 35 (30), 5381-5384). First, compounds of structure 1 can be purchased or prepared according to methods known to those skilled in the art (for an example, see Reaction Scheme 3 below) and reacted with sulfur monochloride (ClSSCl) in an appropriate solvent system, for example pyridine (Py) and diethylether ($Et_2O$), at reduced temperatures to obtain trisulfide compounds of structure 2. Next, compounds of structure 3 can be purchased or prepared according to methods known to those skilled in the art and reacted with compounds of structure 2 in an appropriate solvent system, for example pyridine and diethylether, at reduced temperatures to yield compounds of structure 4. One skilled in the art will appreciate that other compounds of structure (I) wherein n is not 4 can be prepared by modification of the above procedure or through other methods known to those skilled in the art.

Reaction Scheme 3

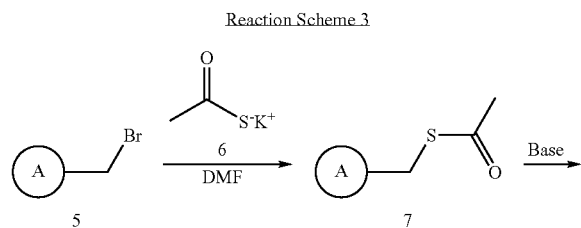

-continued

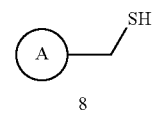

In some embodiments of Reaction Schemes 1 and 2, the $R^1$ of compound 1 is an aralkyl or heteroarylalkyl group. In these embodiments, the compound of structure 1 may be purchased commercially or prepared according to Reaction Scheme 3, wherein A represents an aryl or heteroaryl group. Briefly, compounds of structure 5 can be treated with thioate 6 in an appropriate solvent, such as DMF, to obtain compounds of structure 7. Compounds of structure 7 can then be treated with an appropriate base, such as dimethylamine or potassium carbonate, in an appropriate solvent, such as THF or $H_2O$/methanol, to obtain compounds of structure 8.

Reaction Scheme 4

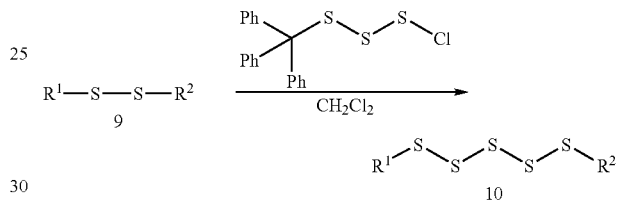

Compounds of structure (I) wherein n is 5 (compound 10) can be prepared by the direct insertion approach (see Hou, Y., Abu-Yousef, I., Harpp, D. Tetrahedron Letters 41 (2000), 7809-7812). Referring to Reaction Scheme 4, wherein $R^1$ and $R^2$ are as defined herein, disulfide compounds of structure 9 are purchased or prepared according to methods known to those skilled in the art and reacted with 1-chloro-3-trityl-trisulfane in an appropriate solvent, such as dichloromethane, to yield pentasulfides of structure 10.

The following examples are provided for purposes of illustration, not limitation.

EXAMPLES

Example 1

Synthesis of Representative Disulfide Compounds

The following disulfide compounds are prepared according to Reaction Scheme 1 described above by the following general procedure: A mixture of sulfur powder (2.5 mmol) and sodium sulfide (5 mmol) in water (1.25 ml) was stirred vigorously for 0.5 h at 50° C., and then cooled to room temperature. To this mixture was added didecyldimethyl-ammonium bromide (DDAB, 4 mol %), followed by addition of a bromide (i.e., $R^1$—Br) (5 mmol) in chloroform (1.25 ml). After stirring at room temperature overnight, this reaction mixture was poured into water (10 ml) and extracted with diethyl ether (15 ml×3). The combined extracts were washed with water (10 ml), dried ($Na_2SO_4$) and evaporated to dryness. The desired disulfide was purified by silica-gel column chromatography with 10% $CH_2Cl_2$/Hexane.

| Cpd. # | Name | Structure | MW |
|---|---|---|---|
| 1-1 | 1,2-diphenyldisulfane | 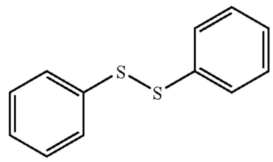 | 218.34 |
| 1-2 | 1,2-dibenzyldisulfane | 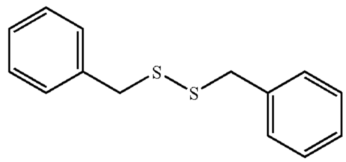 | 246.39 |
| 1-3 | 1,2-bis(4-methylbenzyl)disulfane | 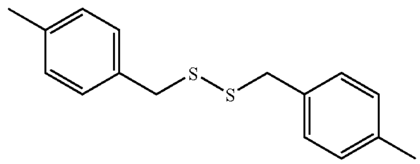 | 274.44 |
| 1-4 | 1,2-bis(3-methylbenzyl)disulfane | 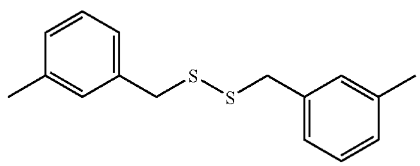 | 274.44 |
| 1-5 | 1,2-bis(2-methylbenzyl)disulfane | 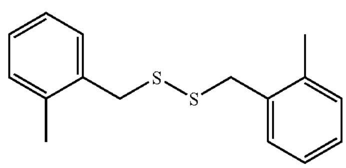 | 274.44 |
| 1-6 | 1,2-bis(4-chlorobenzyl)disulfane | 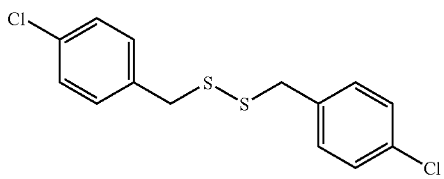 | 315.28 |
| 1-7 | 1,2-bis(3-chlorobenzyl)disulfane | 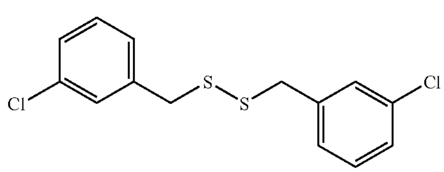 | 315.28 |
| 1-8 | 1,2-bis(2-chlorobenzyl)disulfane | 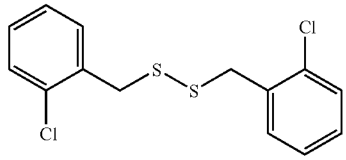 | 315.28 |
| 1-9 | 2,2'-disulfanediylbis(1-phenylethanone) | 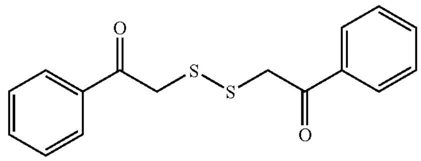 | 302.41 |

-continued

| Cpd. # | Name | Structure | MW |
| --- | --- | --- | --- |
| 1-10 | 1,2-di(p-tolyl)disulfane | 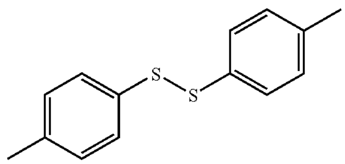 | 246.39 |
| 1-11 | 1,2-di(m-tolyl)disulfane | 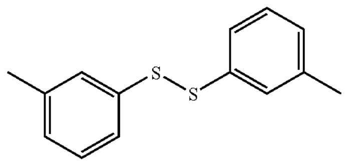 | 246.39 |
| 1-12 | 1,2-di(o-tolyl)disulfane | 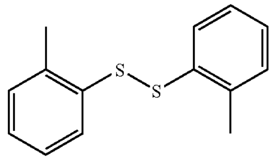 | 246.39 |
| 1-13 | 1,2-di(pyridin-2-yl)disulfane | 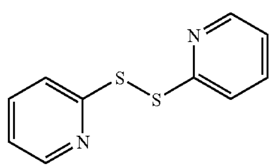 | 220.31 |

Example 2

Synthesis of Representative Trisulfide Compounds

The following trisulfide compounds are prepared according to Reaction Scheme 2 described above.

| Cpd. # | Name | Structure | MW |
| --- | --- | --- | --- |
| 2-1 | 1,3-dibenzyltrisulfane | 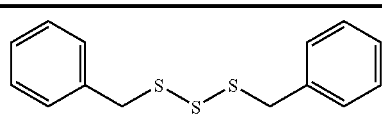 | 278.46 |
| 2-2 | 1,3-diphenyltrisulfane | 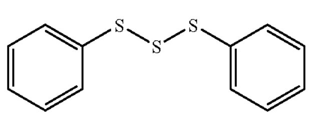 | 250.40 |

Example 3

Synthesis of Representative Tetrasulfide Compounds

The following tetrasulfide compounds are prepared according to Reaction Scheme 2, described above, wherein $R^1$ and $R^2$ are as defined herein, by the following general procedure: A solution of a mercaptan (i.e., $R^1$—SH) (5 mmol) and pyridine (5 mmol) in anhydrous diethylether (12.5 ml) was added dropwise over 0.5 h to a stirred solution (−78° C.) of sulfur monochloride (5 mmol) in 25 ml of anhydrous ether. The reaction mixture was stirred at −78° C. for 0.5 h under argon before the addition of a second mercaptan (i.e., $R^2$—SH) (5 mmol) and pyridine (5 mmol) in anhydrous diethylether (12.5 ml). After stirring at −78° C. for another 0.5 h, the reaction was quenched by addition of water (25 ml), and allowed to warm to room temperature. The organic layers were separated, and washed with water (25 ml) several times until the pH of the aqueous washing was around neutral. The organic layers were evaporated to dryness. The desired polysulfide was purified by either silica-gel column chromatography, recrystallization from hexane, or preparative HPLC (Column: Phenomenex, 250×10 mm, 10 micro, Luna 10μ)

| Cpd. # | Name | Structure | MW |
|---|---|---|---|
| 3-1 | 1,4-dibenzyltetrasulfane | 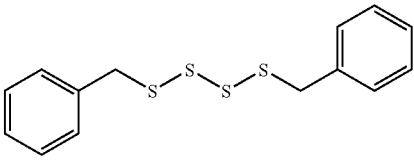 | 310.52 |
| 3-2 | 1,4-bis(4-chlorobenzyl)tetrasulfane | 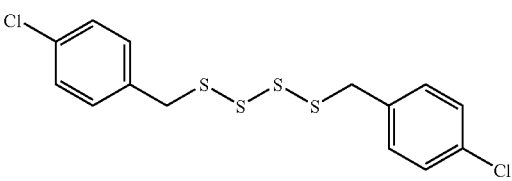 | 379.41 |
| 3-3 | 1,4-bis(2-chlorobenzyl)tetrasulfane | 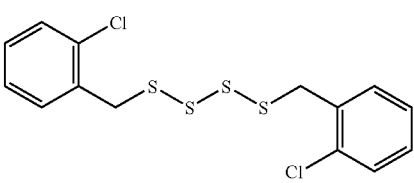 | 379.41 |
| 3-4 | 1,4-bis(4-methylbenzyl)tetrasulfane | 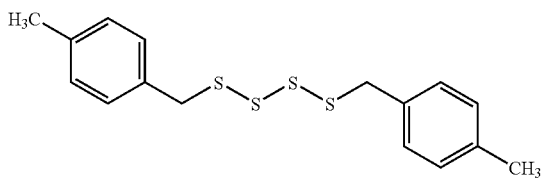 | 338.57 |
| 3-5 | 1,4-bis(3-methylbenzyl)tetrasulfane | 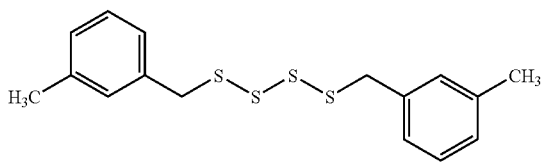 | 338.57 |
| 3-6 | 1,4-bis(2-methylbenzyl)tetrasulfane | 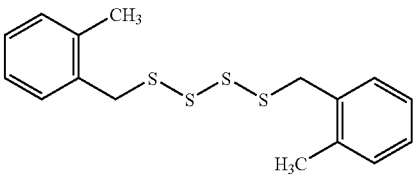 | 338.57 |
| 3-7 | 1,4-diphenethyltetrasulfane | 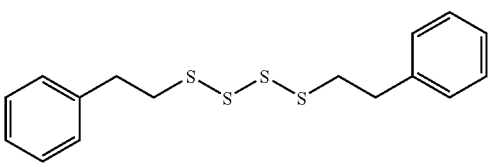 | 338.57 |
| 3-8 | 1,4-diphenyltetrasulfane | 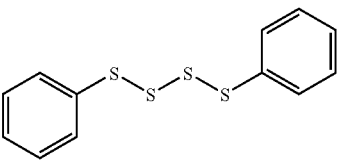 | 282.47 |
| 3-9 | 3,3'-tetrasulfanediylbis(methylene) dibenzoic acid | 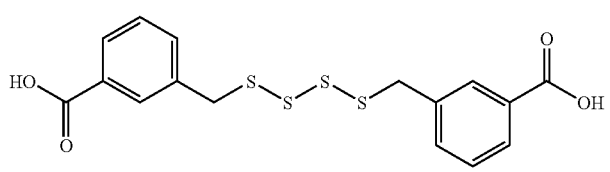 | 398.54 |

-continued

| Cpd. # | Name | Structure | MW |
|---|---|---|---|
| 3-10 | 4,4'-tetrasulfanediylbis(methylene)dianiline | H₂N–C₆H₄–CH₂–S–S–S–S–CH₂–C₆H₄–NH₂ | 340.55 |
| 3-11 | 1,4-bis((1H-imidazol-4-yl)methyl)tetrasulfane | (1H-imidazol-4-yl)–CH₂–S–S–S–S–CH₂–(1H-imidazol-4-yl) | 290.45 |
| 3-12 | 1,4-bis(oxazol-4-ylmethyl)tetrasulfane | (oxazol-4-yl)–CH₂–S–S–S–S–CH₂–(oxazol-4-yl) | 292.42 |
| 3-13 | 1,4-bis((2H-tetrazol-5-yl)methyl)tetrasulfane | (2H-tetrazol-5-yl)–CH₂–S–S–S–S–CH₂–(2H-tetrazol-5-yl) | 294.40 |
| 3-14 | 1,4-bis((1-benzyl-1H-imidazol-4-yl)methyl)tetrasulfane | (1-benzyl-1H-imidazol-4-yl)–CH₂–S–S–S–S–CH₂–(1-benzyl-1H-imidazol-4-yl) | 470.70 |
| 3-15 | 3,3'-tetrasulfanediyl dibenzoic acid | HOOC–C₆H₄–S–S–S–S–C₆H₄–COOH | 370.49 |
| 3-16 | 4,4'-tetrasulfanediyl dianiline | H₂N–C₆H₄–S–S–S–S–C₆H₄–NH₂ | 312.50 |
| 3-17 | 1,4-di(1H-imidazol-4-yl)tetrasulfane | (1H-imidazol-4-yl)–S–S–S–S–(1H-imidazol-4-yl) | 262.40 |

| Cpd. # | Name | Structure | MW |
|---|---|---|---|
| 3-18 | 1,4-di(oxazol-4-yl)tetrasulfane | 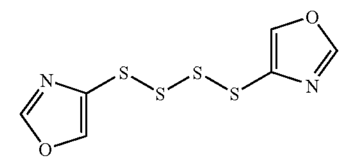 | 264.37 |
| 3-19 | 1,4-di(2H-tetrazol-5-yl)tetrasulfane | 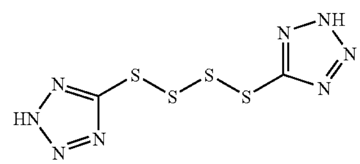 | 266.35 |
| 3-20 | 1,4-bis(1-benzyl-1H-imidazol-4-yl)tetrasulfane | 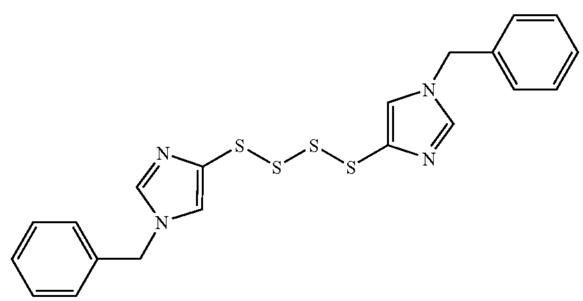 | 442.64 |
| 3-21 | 1,4-bis((6-ethylpyridin-3-yl)methyl)tetrasulfane | 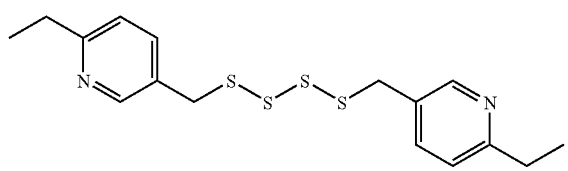 | 368.60 |
| 3-22 | 1,4-bis(pyridin-3-ylmethyl)tetrasulfane | 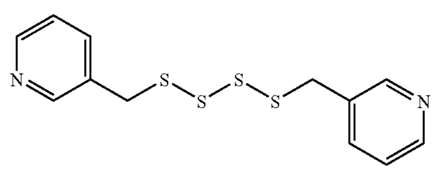 | 312.5 |
| 3-23 | 1,4-bis(3-chlorobenzyl)tetrasulfane | 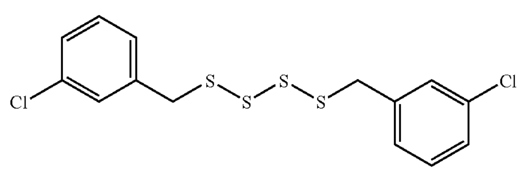 | 315.28 |
| 3-24 | 3,3'-tetrasulfanediylbis(methylene)dianiline | 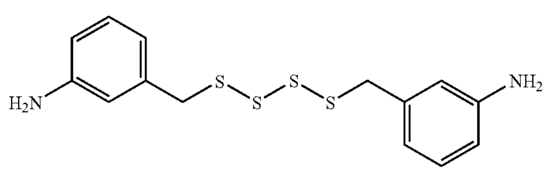 | 340.55 |
| 3-25 | 2,2'-tetrasulfanediylbis(methylene)dianiline | 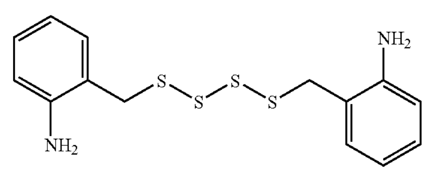 | 340.55 |

-continued

| Cpd. # | Name | Structure | MW |
|---|---|---|---|
| 3-26 | 3,3'-tetrasulfanediyldianiline | 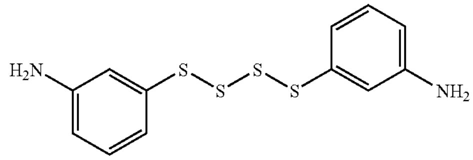 | 312.50 |
| 3-27 | 2,2'-tetrasulfanediyldianiline | 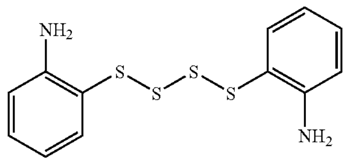 | 312.50 |

Example 4

Pentasulfide Compounds of the Invention

The following pentasulfide compounds are prepared according to Reaction Scheme 4 described above.

| Cpd. # | Name | Structure | MW |
|---|---|---|---|
| 4-1 | 1,5-dibenzylpentasulfane | 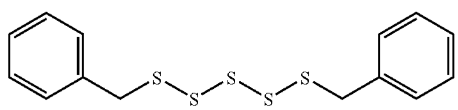 | 342.59 |
| 4-2 | 1,5-diphenylpentasulfane | 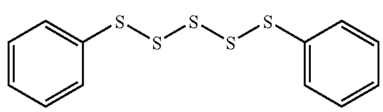 | 314.53 |

Example 5

Analysis of Sulfide Release from Polysulfide Compounds in Hepes Buffer Via Monobromobimane Derivatization Compounds (3-1), (3-2), and (3-3) were dissolved in 90/10 ethanol/PEG (polyethylene glycol)-300+0.1% TFA (trifluoroacetic acid) to a concentration of 40 mM. This stock solution was further diluted in HEPES buffer (50 mM, pH 8.0) to a concentration of 4.2 mM. The test compounds were then added to HEPES (50 mM, pH 8M) at a final concentration of 385 μM. 200 μl of the HEPES with or without test compound was added to a glass vial containing 200 μl Monobromobimane (10 mM) and 200 μl HEPES (50 mM, pH 8.0) at the following timepoints after addition of test compound: 10 min, 30 min and 120 min. Vials were incubated on an orbital shaker for exactly 10 min, followed by the addition of 2 ml of ethyl acetate and tumbling for a minimum of 10 min. The vials were then centrifuged for 7-10 min at 1200 rpm, followed by transfer of 1 ml of the organic phase into an evaporation vial. The organic phase was then dried down under a stream of nitrogen, taken up in acetonitrile and analyzed by HPLC. Sulfide concentration at various incubation times is shown in FIG. 1.

Example 6

Figure 2:
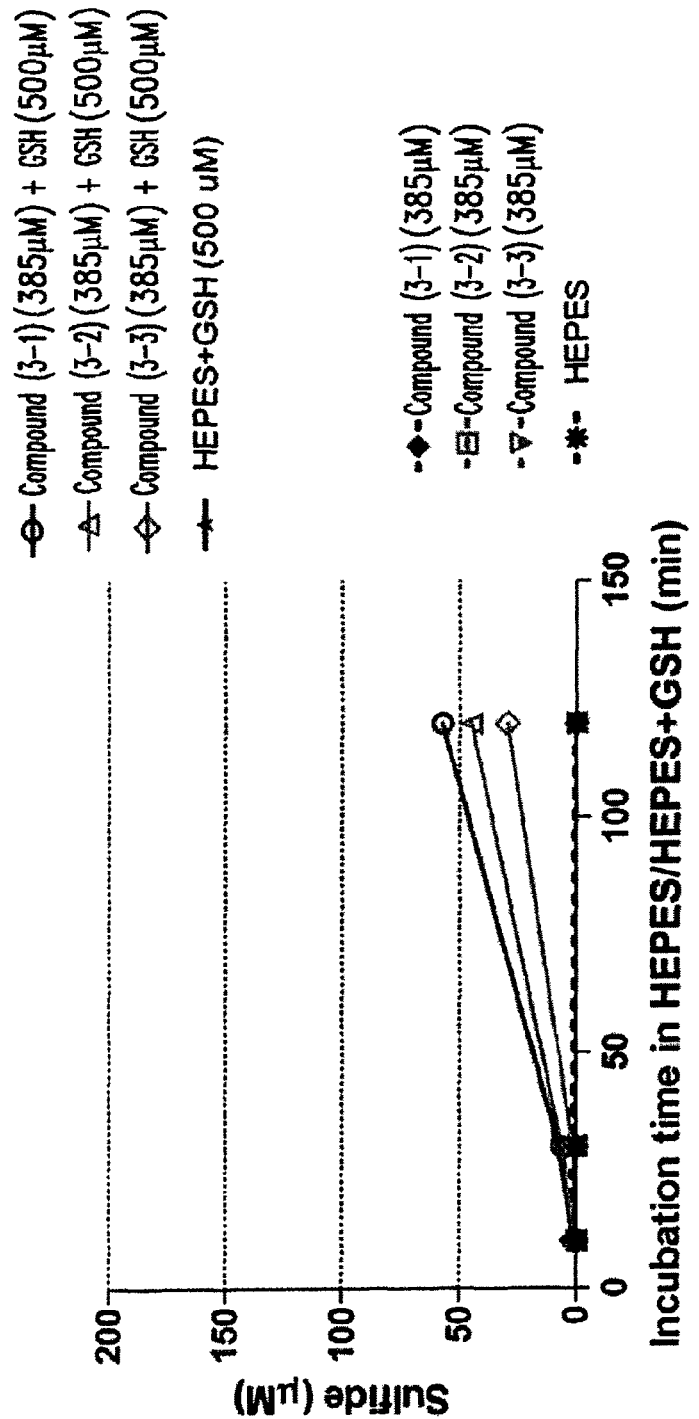
FIG. 2 shows analysis of sulfide release from polysulfide compounds in HEPES buffer and glutathione via monobromobimane derivatization.
Figure 3:
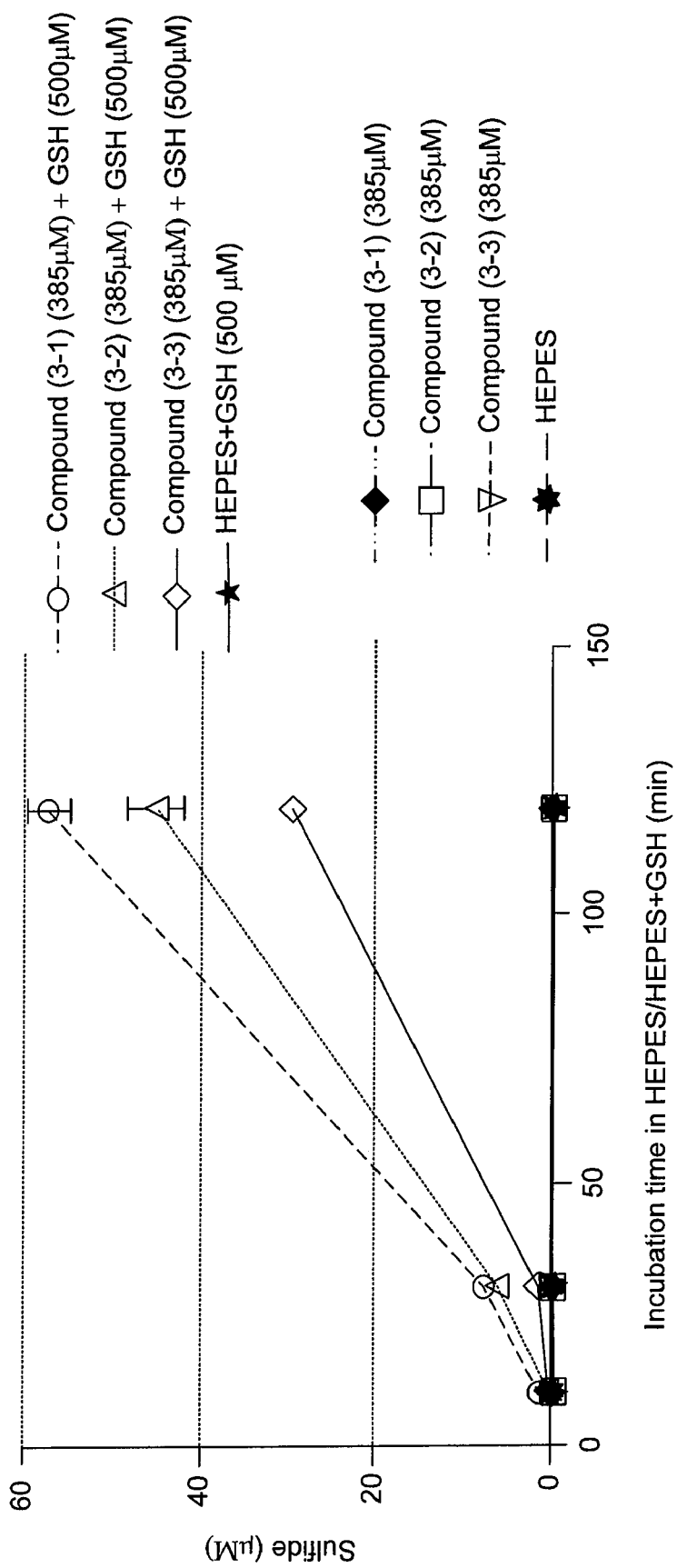
FIG. 3 shows analysis of sulfide release from polysulfide compounds in HEPES buffer and glutathione via monobromobimane derivatization.

Analysis of Sulfide Release from Polysulfide Compounds in Buffer+Glutathione Via Monobromobimane Derivatization Compounds (3-1), (3-2), and (3-3) were dissolved in 90/10 ethanol/PEG (polyethylene glycol)-300+0.1% TFA (trifluoroacetic acid) to a concentration of 40 mM. This stock solution was further diluted in HEPES buffer (50 mM, pH 8.0) to a concentration of 4.2 mM. The test compounds were then added to HEPES or HEPES+Glutathione (GSH, 500 uM) at a final concentration of 385 μM. 200 μl of the HEPES/HEPES+GSH with or without test compound was added to a glass vial containing 200 μl Monobromobimane (10 mM) and 200 μl HEPES (50 mM, pH 8.0) at the following timepoints after the addition of test compound: 10 min, 30 min and 120 min. Vials were incubated on an orbital shaker for exactly 10 min, followed by the addition of 2 ml of ethyl acetate and tumbling for a minimum of 10 min. The vials were then centrifuged for 7-10 min at 1200 rpm, followed by transfer of 1 ml of the organic phase into an evaporation vial. The organic phase was then dried down under a stream of nitrogen, taken up in acetonitrile and analyzed by HPLC. Sulfide concentration at various incubation times is shown in FIGS. 2 and 3.

Example 7

Analysis of Sulfide Release from Polysulfide Compounds in Buffer+Glutathione Via $H_2S$ Probe The instrument serving as the reaction vessel was a closed chamber respirometer (Oroboros oxygraph O2k). The respirometer had dual 16 mm ID pyrex chambers each fitted with a polarographic oxygen sensor (POS) near the chamber floor to monitor solution oxygen concentration, and each has a 15.8 mm OD PVDF or PEEK stopper, materials that exhibit limited oxygen memory, and that can be inserted to adjust chamber volume from 1 to 5 mL. The stoppers had a 1 mm diameter injection port and two 2.5 mm ports to hold a PHSS and a pH electrode. When inserted into the chamber any air or gas above the liquid phase was removed from the chamber through the injection port leaving only a liquid solution in the chamber.

Figure 4:
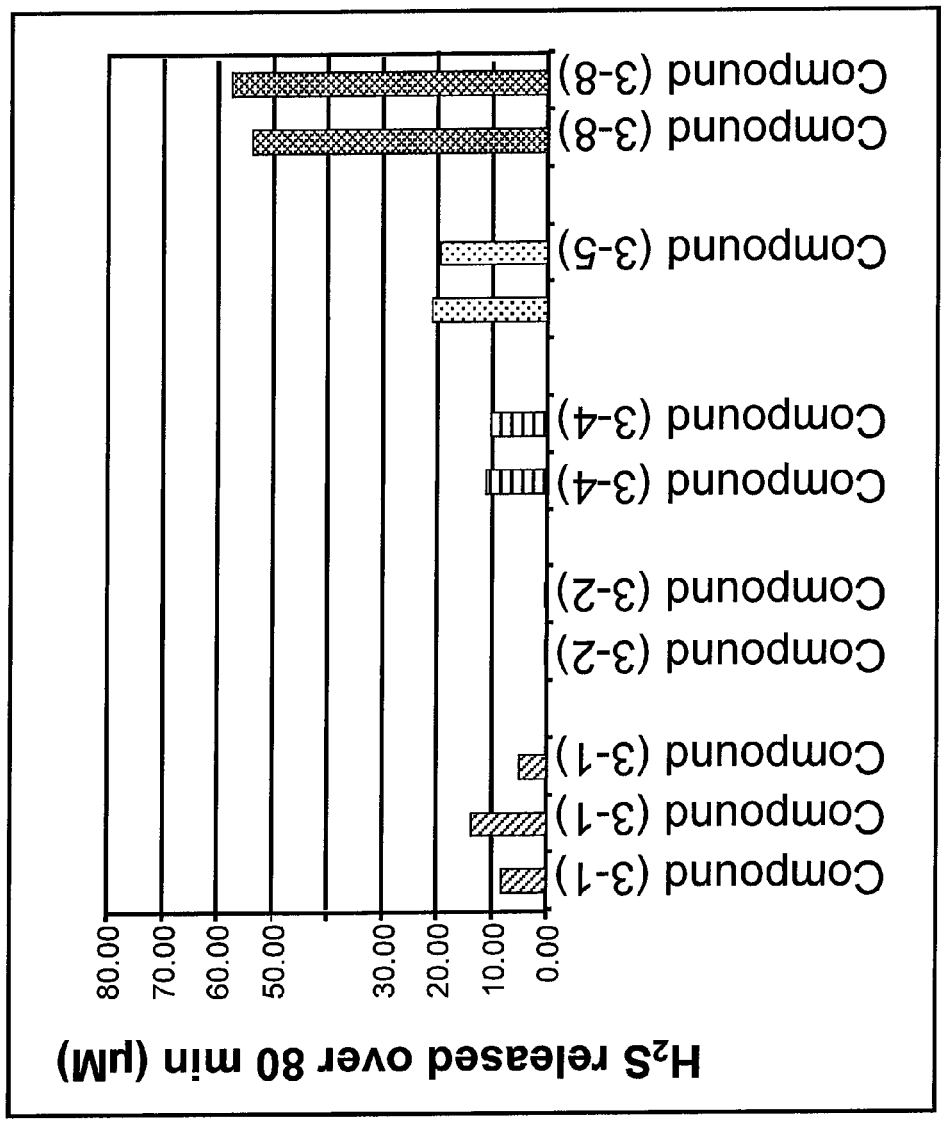
FIG. 4 shows analysis of sulfide release from polysulfide compounds in the presence of glutathione via solid-state sulfide probe.

The protocol for assaying sulfide releasing compounds (SRC) was to first calibrate the PHSS with $Na_2S$ in the chamber filled with 2 mL of anoxic phosphate buffered saline (PBS) containing 50 µM DPTA by making serial additions of the sulfide stock from 0.5 to 40 µM. Once the calibration was complete the chamber solution was first replaced with anoxic PBS and DPTA, then the SRC of interest was added at a concentration near 400 µM to obtain a background rate of $H_2S$ release, usually negligible rates were observed. After approximately 5 minutes an injection of 500 µM glutathione (GSH) was made to catalyze $H_2S$ release. The reaction of the reductant GSH with the SRC in effect disassembled the polythiol SRC thereby releasing $H_2S$ into solution which was measured with the PHSS. The initial rate of $H_2S$ release, the magnitude of $H_2S$ in the chamber when release was complete, and the duration of release were all obtained to characterize each SRC. The amount of $H_2S$ release over 80 minutes for various compounds is tabulated in FIG. 4.

Example 8

Figure 5:
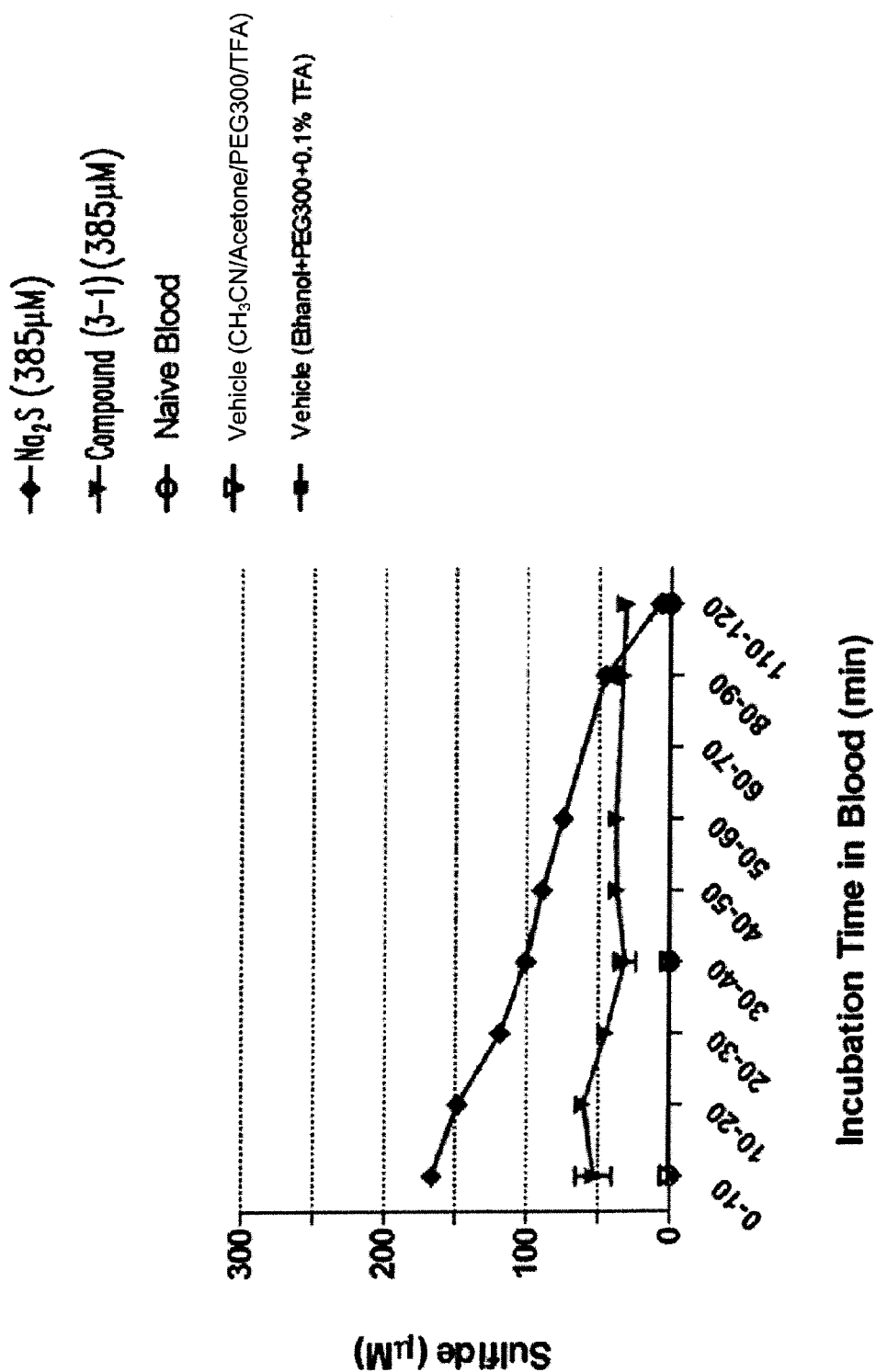
FIG. 5 shows analysis of sulfide release from polysulfide compounds in fresh rat blood via monobromobimane derivatization.
Figure 6:
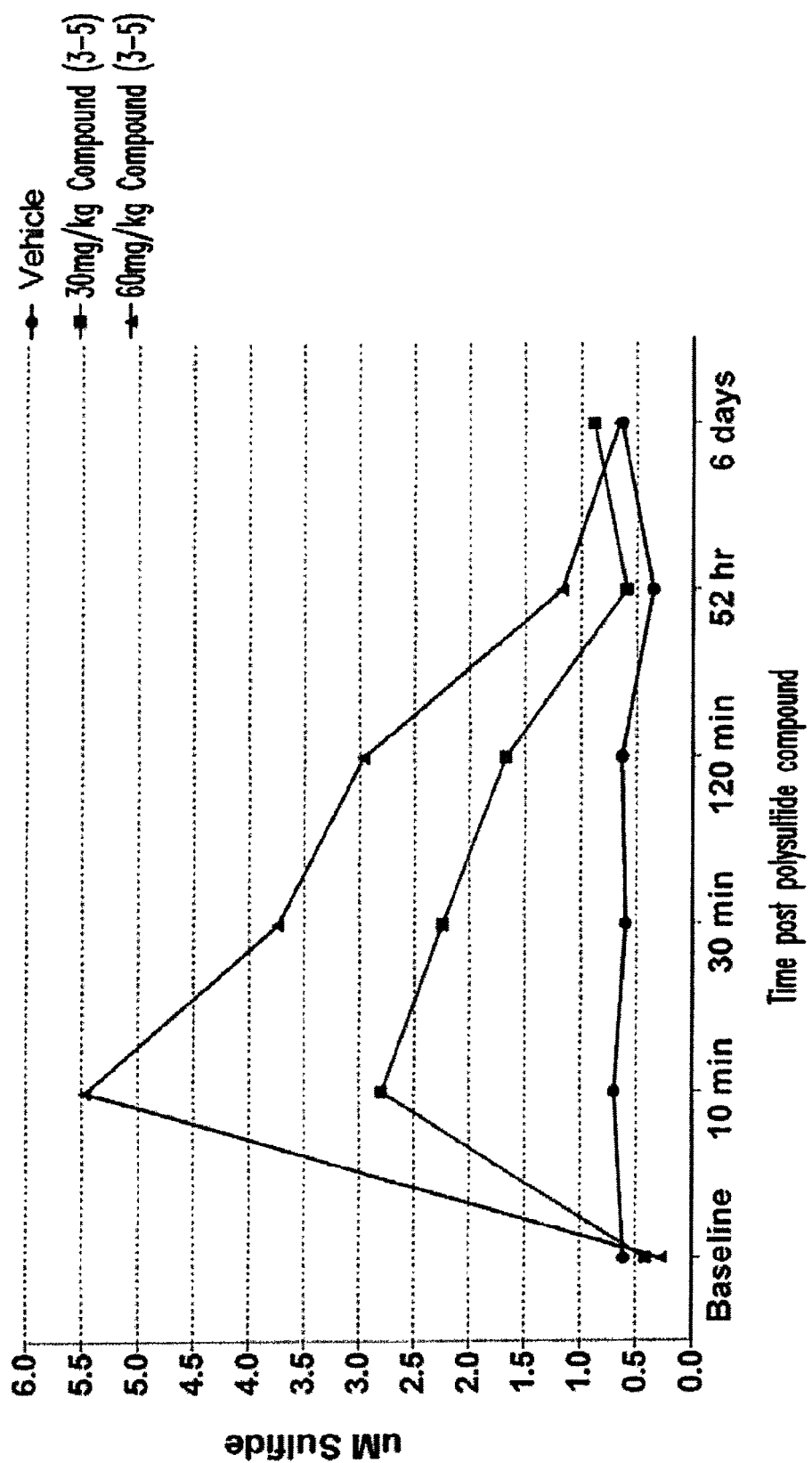
FIG. 6 shows blood sulfide concentration in rats dosed with a polysulfide compound.
Figure 7:
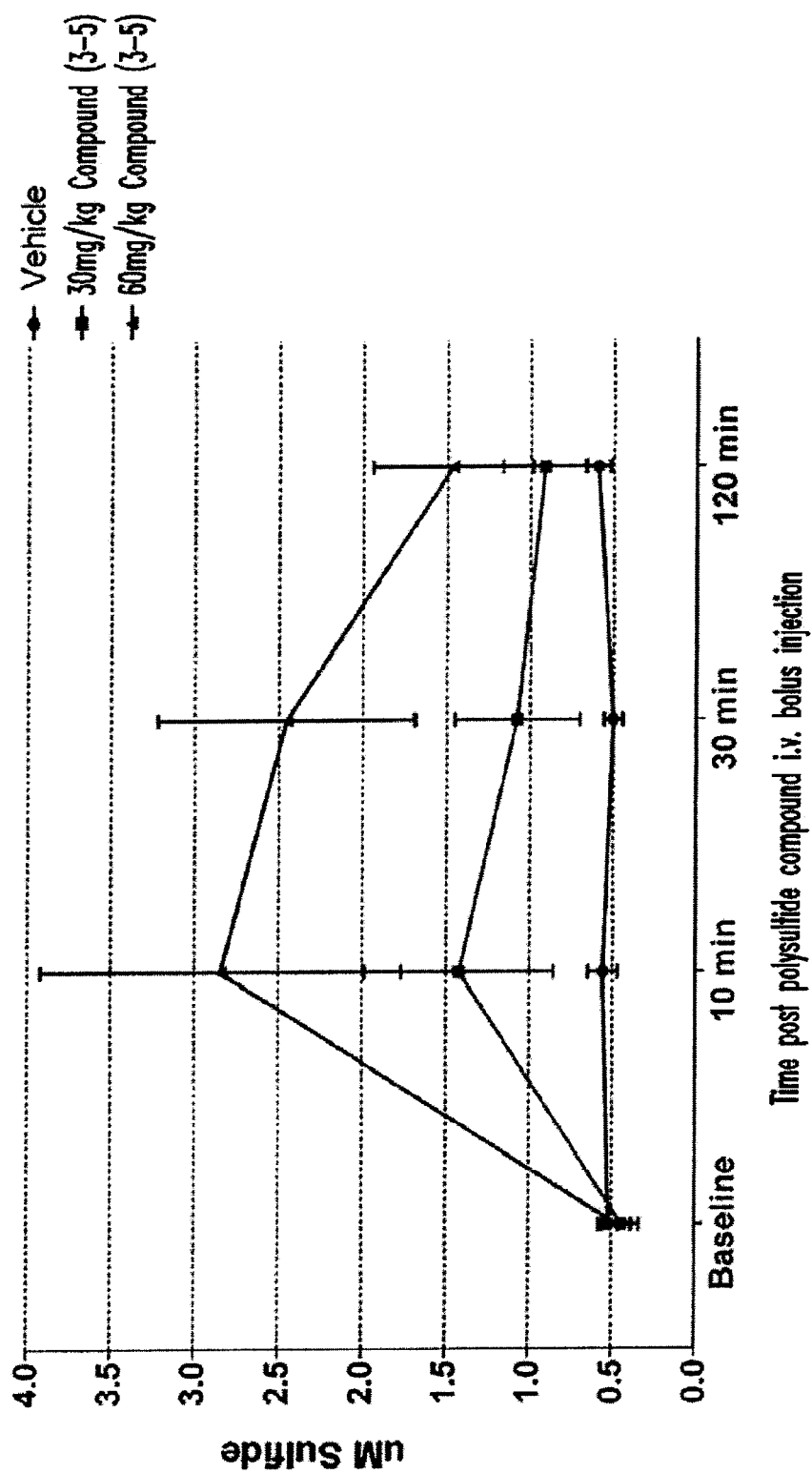
FIG. 7 shows blood sulfide concentration in rats dosed with a polysulfide compound.
Figure 8:
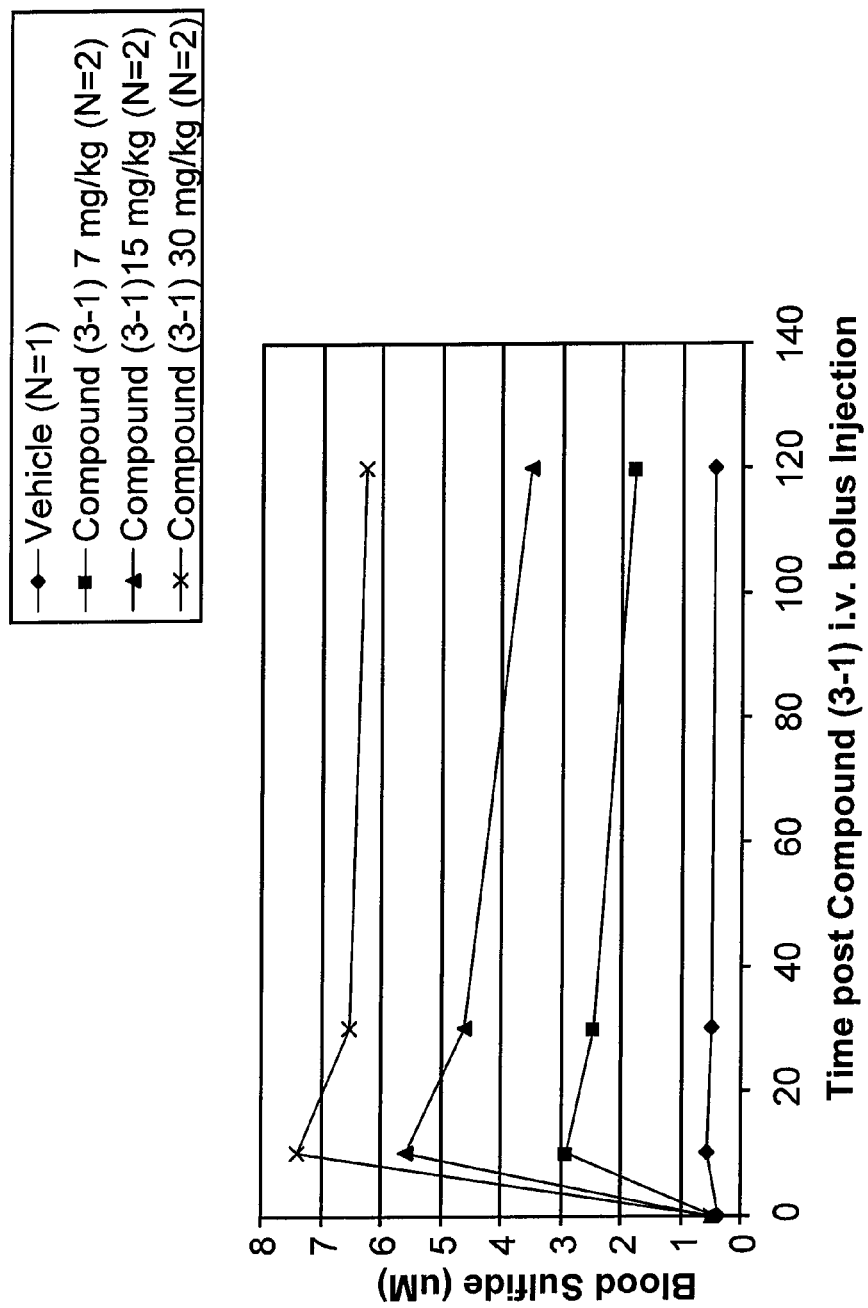
FIG. 8 shows blood sulfide levels in rats dosed with a polysulfide compound as measured by derivatization with monobromobimane.
Figure 9:
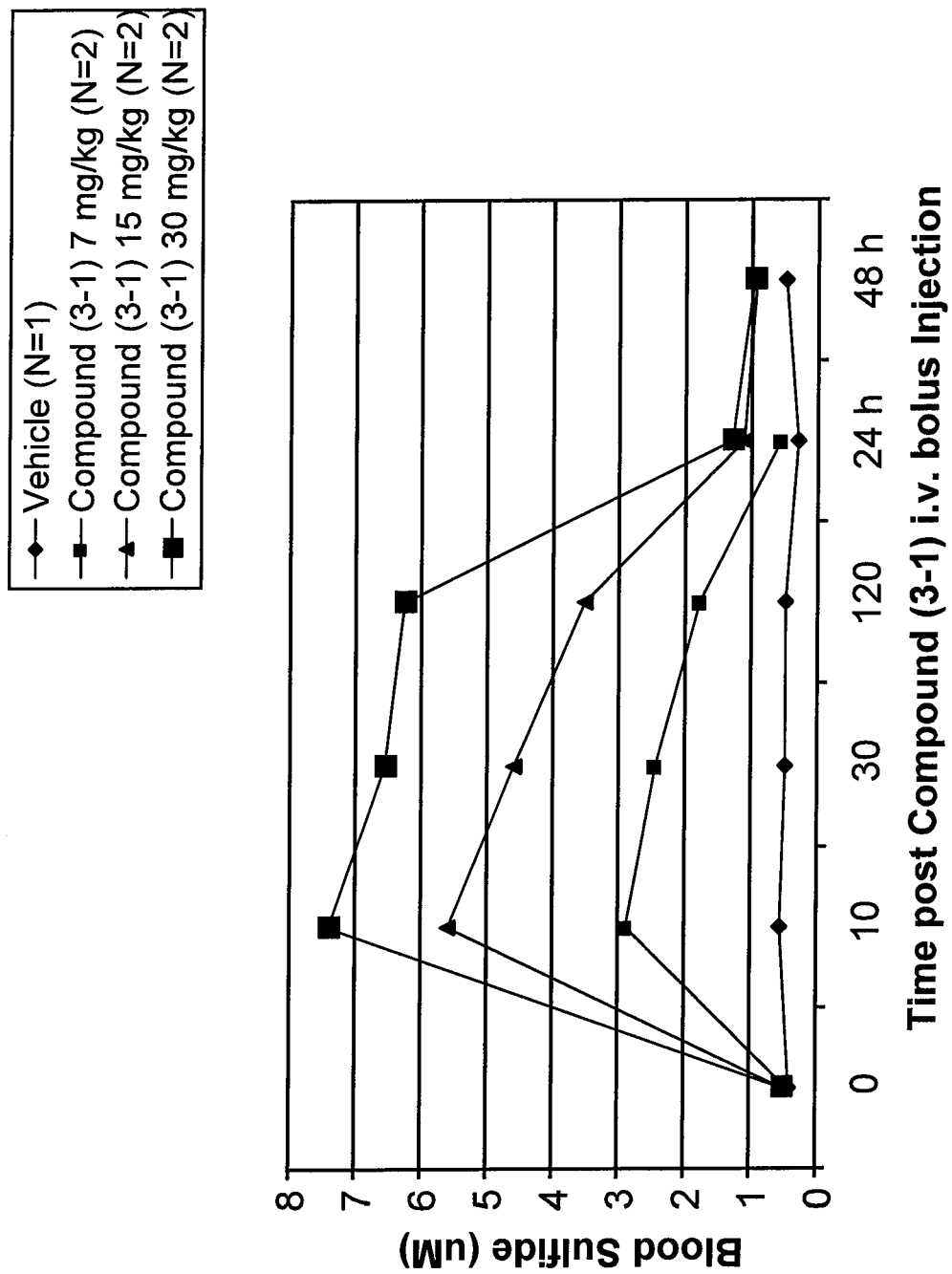
FIG. 9 shows blood sulfide levels in rats dosed with a polysulfide compound as measured by derivatization with monobromobimane.
Figure 10:
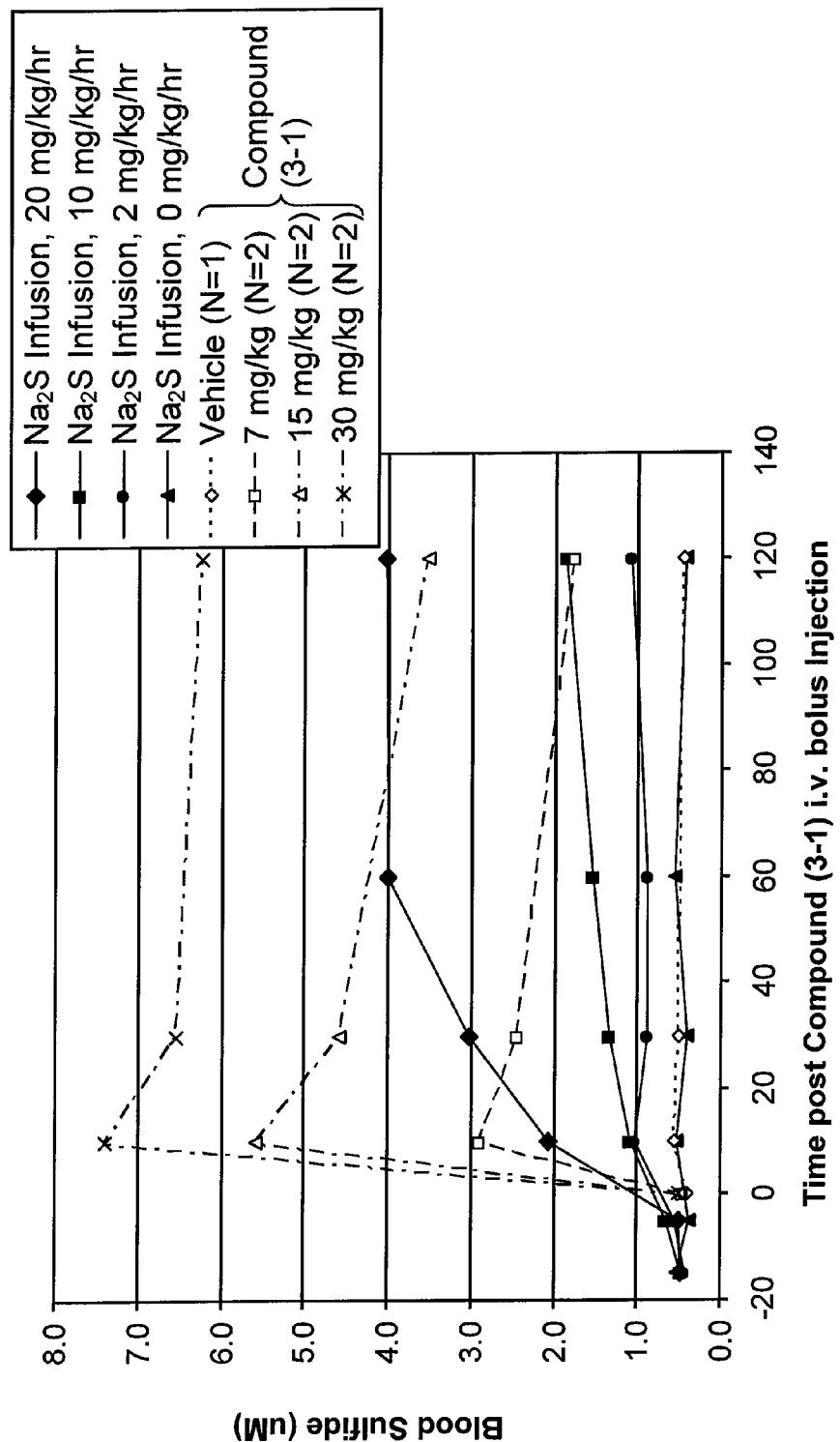
FIG. 10 shows blood sulfide levels in rats dosed with a polysulfide compound as measured by derivatization with monobromobimane.
Figure 11:
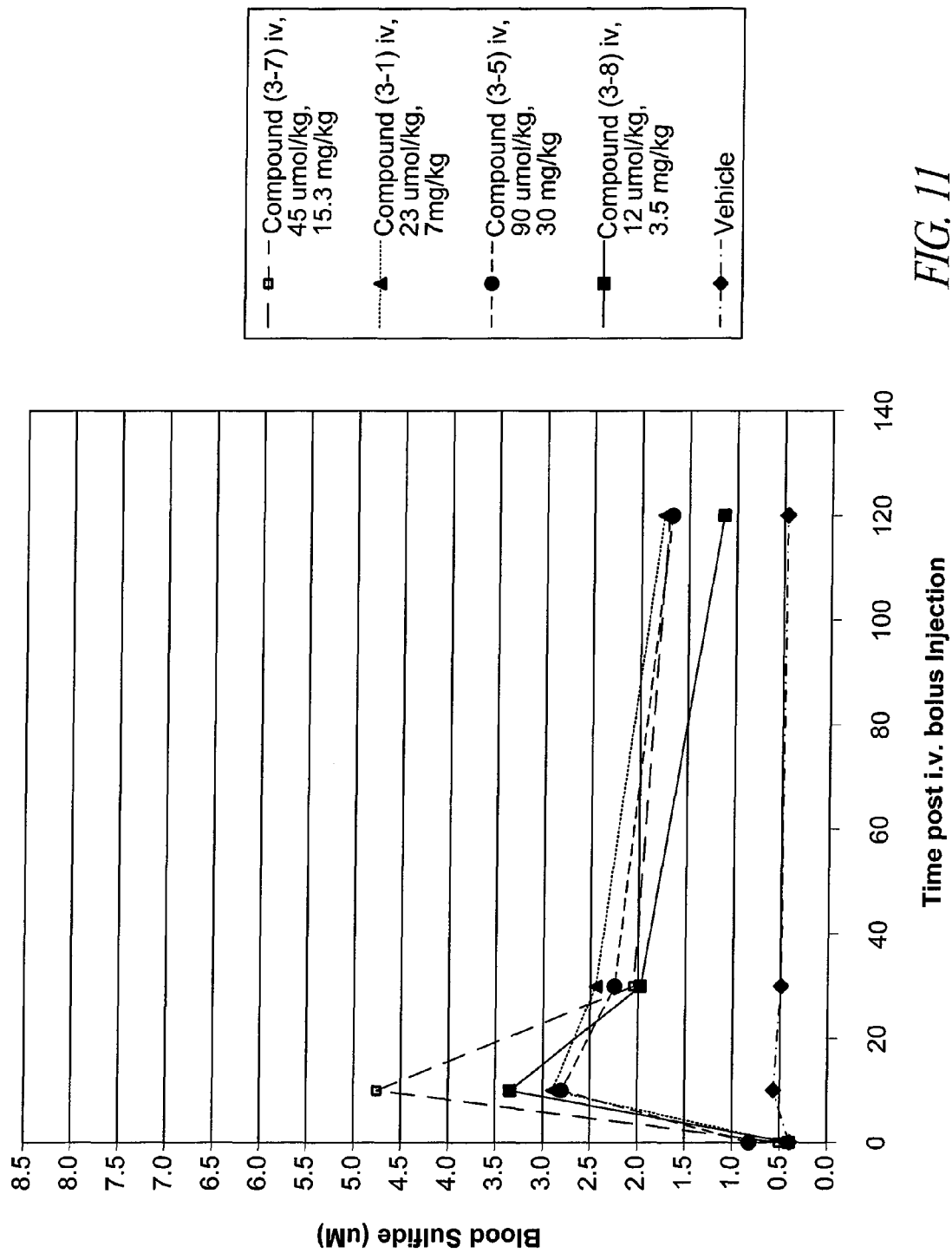
FIG. 11 shows blood sulfide levels in rats dosed i.v. with different polysulfide compounds as measured by derivatization with monobromobimane.

Analysis of Sulfide Release from Polysulfide Compounds in Fresh Rat Blood Via Monobromobimane Derivatization Compounds (3-1), (3-2), and (3-3) were dissolved in 90/10 ethanol/PEG (polyethylene glycol)-300+0.1% TFA (trifluoroacetic acid) to a concentration of 40 mM. This stock solution was further diluted in HEPES buffer (50 mM, pH 8.0) to a concentration of 4.2 mM. Sodium sulfide was diluted in 0.9% NaCl to a concentration of 4.2 mM. Test compounds were then added to fresh rat blood at a final concentration of 385 µM. Blood was also spiked with dilution vehicle (90/10 ethanol/PEG-300+0.1% TFA or 40/40/20 acetonitrile/acetone/PEG-300+0.1% TFA) as a control. 200 µl of the blood spiked with test compound, was added to a glass vial containing 200 µl Monobromobimane (10 mM) and 200 µl HEPES (50 mM, pH 8.0) at the following timepoints after spiking: 0 min, 10 min, 20 min, 30 min, 40 min, 50 min, 60 min, 80 min and 110 min. Naïve blood or blood spiked with vehicle was added to the reaction mix at the following timepoints: 0 min, 30 min and 110 min. After the addition of naïve/spiked blood or spiked vehicle, vials were incubated on an orbital shaker for exactly 10 min, followed by the addition of 2 ml of ethyl acetate and tumbling for a minimum of 10 min. The vials were then centrifuged for 7-10 min at 1200 rpm, followed by transfer of 1 ml of the organic phase into an evaporation vial. The organic phase was then dried down under a stream of nitrogen, taken up in acetonitrile and analyzed by HPLC. Sulfide concentration at various incubation times is shown in FIG. 5.

Example 9

Detection of Sulfide in Rat Blood Following Administration of Polysulfide Compounds Sulfide levels were measured in rat blood following dosing of Compounds (3-1), (3-5), (3-7), (3-8) or sodium sulfide. Results are shown in FIGS. 6-11. The following example demonstrates dosing of compound (3-1) in rats. Experiments were conducted with groups of three to four animals consisting of 9-10 week-old, male Sprague Dawley rats, (276-300) grams (Charles River Laboratory, Boston Mass.) with a jugular vein catheter (JVC) and a femoral vein catheter (FVC)). Animals were allowed to recover and acclimate in a temperature and humidity controlled environment for 1-3 days prior to the commencement of experimental procedures. Food and water were provided ad libitum.

A baseline blood sample (~0.4 ml) was collected from each rat through the jugular veincannula into a heparin-coated 1 ml syringe fitted with a 23 g Luer stub adapter. After sampling, a corresponding volume of 20:1 saline to heparin was slowly injected into the animal through the jugular vein cannula,. A bolus dose of Compound (3-1) (7.5 mg/kg i.v., 15 mg/kg i.v., 30 mg/kg i.v., or 60 mg/kg i.v), in vehicle (EtOH/PEG300 +0.1% citric acid) was injected through the femoral vein catheter. Blood (~0.4 mL) was collected at 10, 30, 120 minutes and 24, 48 hours post dosing via the Jugular vein cannula using a heparin-coated one ml syringe with a 23 g Luer stub adapter. After sampling, a corresponding volume of 20:1 (saline to heparin) was slowly injected into the animal through the Jugular vein cannula.

The blood sample was immediately processed as described herein. Briefly, 200 ul of blood was added to a vial of Monobromobimane derivatization reagents. Vials were placed on an orbital shaker. Ethyl acetate was added to each sample and rotated. Vials were placed on a tumbler for a minimum of 10 minutes but no longer then 60 minutes then centrifuged. A sample of organic phase of each sample was placed in an evaporation vial and dried under nitrogen. Sulfide levels were measured by HPLC were recovered from blood for a 48-hour period. Plots of plasma concentration of compound versus time were constructed. The fundamental pharmacokinetic parameters of compound after IV dosing were obtained from the non-compartmental analysis (NCA) of the plasma data using WinNonlin.Pharmacokinetics analysis software.

Example 10

Determination of Cytoprotective Benefit from Hepatic Injury in the Murine Hepatic Ischemia-Reperfusion Injury Model The ability of compound (3-1) to provide cytoprotective benefit in a model of hepatic ischemia-reperfusion (I/R) injury was tested in mice. In this study, it was demonstrated that intraperitoneal bolus administration of Compound (3-1) post-hepatic ischemia and immediately prior to a five hour reperfusion period decreased liver transaminase alanine aminotransferase (ALT) measured in serum. In contrast, treatment with vehicle did not provide any protective benefits in the hepatic I/R injury.

The mice used in these studies were C57-BL6/J mice, 8-10 weeks, (Jackson Laboratory, Bar Harbor, Me.). Food and water were provided ad libitum. Test animals were allowed to acclimate in a temperature and humidity controlled environment prior to the commencement of experimental procedures.

Mice were anesthetized with ketamine and xylazine and maintained with warming during surgical procedures to induce hepatic ischemia-reperfusion (I/R) injury. Specifically, a midline incision was performed to expose the liver, and heparin was injected to prevent blood clotting. Both the hepatic artery and portal vein were clamped with microaneurysm clamps to render the left lateral and median lobes of the liver ischemic. Ischemia proceeded for 45 minutes, with the liver maintained in the peritoneal cavity in its original location and kept moist with gauze soaked with 0.9% normal saline. Control mice received sham surgeries, although hepatic blood flow was not reduced with a microaneurysm clamp. At the end of 45 minutes, microaneurysm clamps were removed. Serum liver transaminase levels (ALT) were tested after five hours of hepatic reperfusion using spectrophotometry and commercially available reagents (Sigma-Aldrich).

Figure 12:
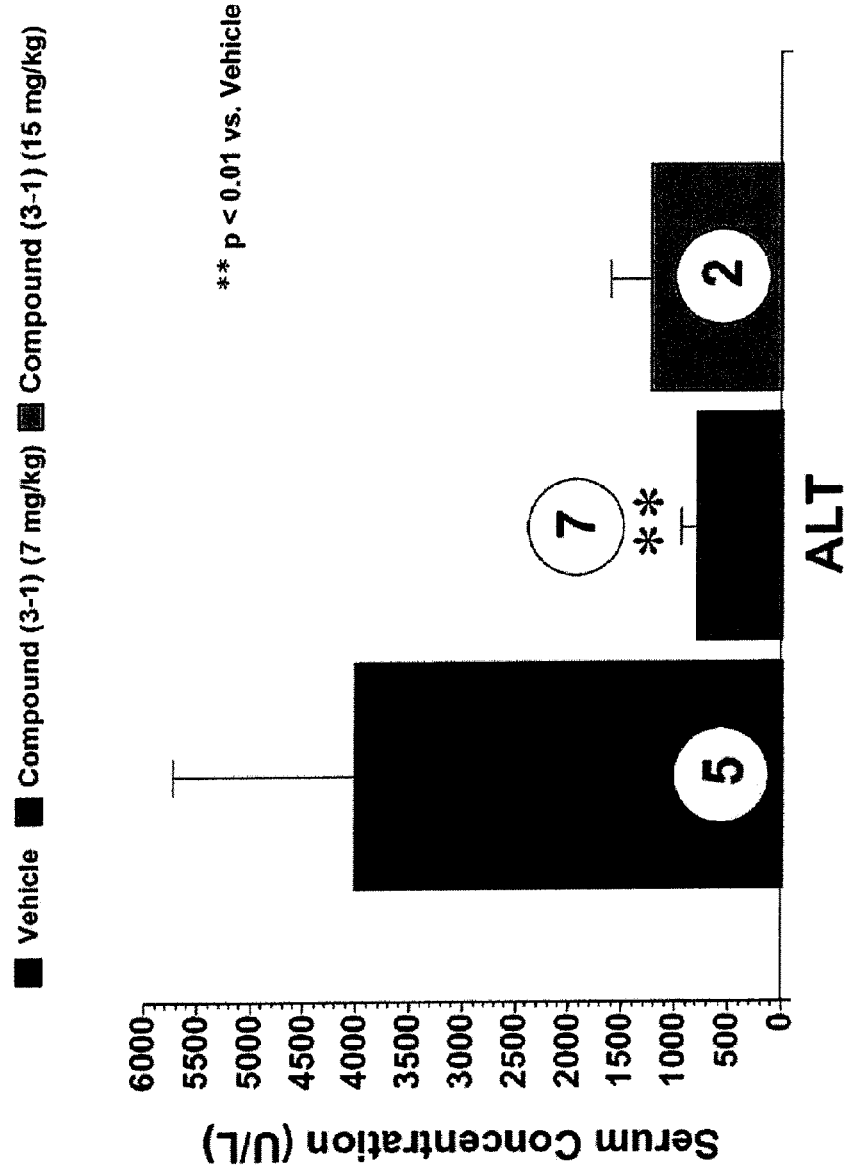
FIG. 12 shows hepatic ischemia-reperfusion injury in rats dosed with a polysulfide compound.

Murine hepatic ischemia-reperfusion injury test animals were randomized to four groups. Group 1: vehicle (EtOH/PEG300+0.1% citric acid) treated; Group 2: treatment with 7 mg/kg Compound (3-1); Group 3: treatment with 15.0 mg/kg Compound (3-1). As shown in FIG. 12, ALT levels achieved statistically significant reduction at 7 mg/kg. ALT levels were reduced in the two treatment groups (7.0 mg/kg, and 15.0 mg/kg), compared to vehicle.

Example 11

Cardioprotective Benefit in the Murine Myocardial Ischemia Reperfusion Model

The ability of compound (3-1) to provide cardioprotective benefits in a myocardial ischemia-reperfusion (I/R) injury model was tested in mice. In this study, it is shown that bolus administration of compound (3-1) into the left ventricular cavity post-ischemia and five minutes prior to a 24-hour reperfusion period reduced myocardial ischemia and reduced myocardial infarct size as a percentage of risk area. The mice used in these studies were C57-BL6/J mice, 8-10 weeks, (Jackson Laboratory, Bar Harbor, Me.). Food and water were provided ad libitum. Test animals were allowed to acclimate in a temperature and humidity controlled environment prior to the commencement of experimental procedures.

Mice were anesthetized with ketamine and pentobarbital sodium and maintained with warming during surgical procedures to induce myocardial ischemia-reperfusion (I/R) injury. Mice were placed on a surgical board ventral side, orally intubated and connected to a Model 683 rodent ventilator (Tidal volume: 2.2 mLs, respiratory rate: 122 breaths per minute with 100% oxygen supplementation via the ventilator side port) (Harvard Apparatus). The chest was opened and the proximal left main coronary artery was exposed and ligated. Myocardial and coronary artery occlusion was maintained for 30 minutes, followed by removal of the suture and reperfusion for 24 hours.

After 24 hours of reperfusion, post-ischemia, mice were anesthetized, intubated, and connected to a rodent ventilator. Evans blue dye was injected into a catheter threaded in the common carotid artery. A median sternotomy was performed and the left main coronary artery was re-ligated in the same location as the previous ligation. The separation of the ischemic zone from nonischemic zone was visualized with Evans Blue dye, the heart was rapidly excised and serially sectioned along the short axis in five 1-mm sections that were incubated in 1.0% 2,3,5-triphenyltetrazolium chloride (Sigma-Aldrich) for five minutes at 37° C. to separate the viable and nonviable myocardium within the risk zone. Each of the five myocardial slices (1-mm) were weighed, areas of infarction, area at risk (AAR), and non-ischemic left ventricle were assessed with computer-assisted planimetry by an observer blinded to sample identity. For procedures for the left ventricular area at risk (AAR) and infarct size determination see Jones, S. P. et al. Am. J. Physiol. Heart Circ. Physiol. (2004) 286:H276-H282.

Data were analyzed by 2-way ANOVA with post-hoc Bonferroni analysis using StatView software version 5.0 (SAS Institute). Data are reported as mean±SEM. p values less than 0.05 were considered significant.

Figure 13:
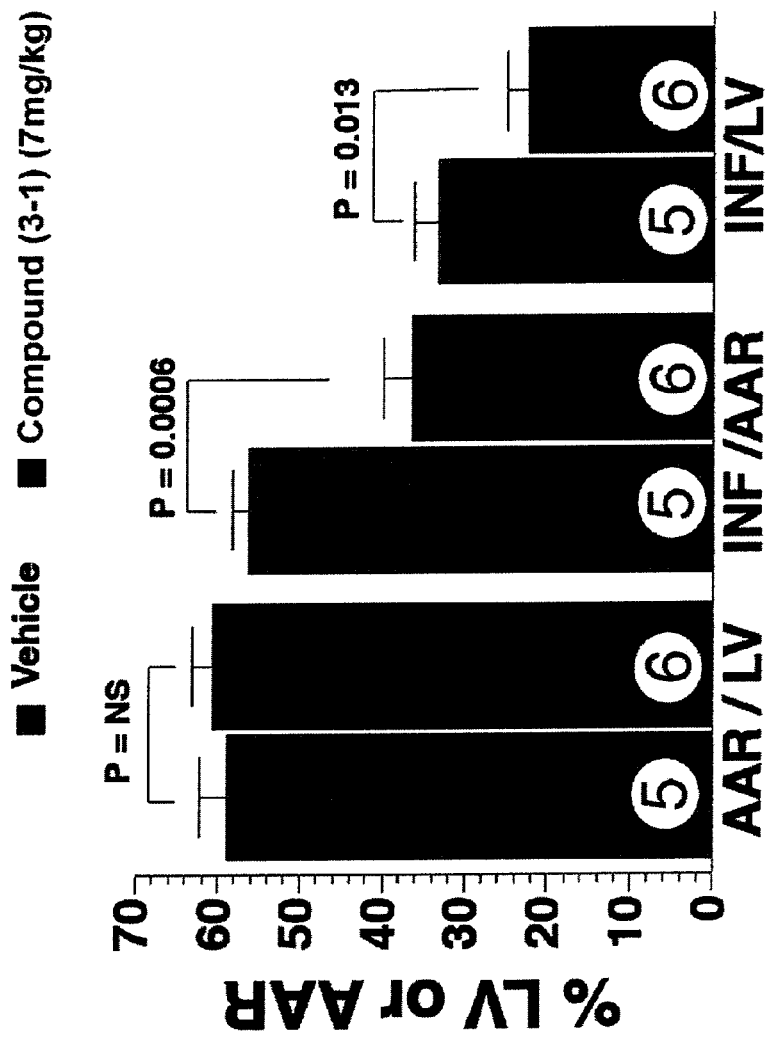
FIG. 13 shows myocardial infarct size in rats dosed with a polysulfide compound.

Murine myocardial ischemia reperfusion model test groups of 10-13 animals were randomized to four treatment groups. Group 1: vehicle (EtOH/PEG300+0.1% citric acid) treated; and Group 2: treatment with 7 mg/kg Compound (3-1). In this study, bolus administration of Compound (3-1) into the left ventricular cavity after 30 minutes ischemia and five minutes prior to a 24 hour reperfusion period reduced myocardial infarct size as a percentage of risk area (FIG. 13). Vehicle did not provide any protective benefits in the myocardial I/R injury.

All of the U.S. patents, U.S. patent application publications, U.S. patent applications, foreign patents, foreign patent applications and non-patent publications referred to in this specification are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound having one of the following structures:

(1-6)

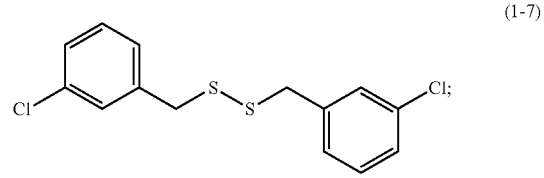

(1-7)

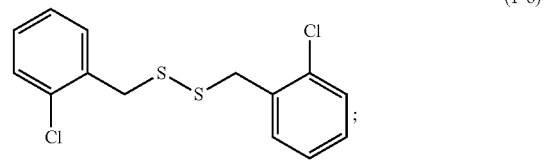

(1-8)

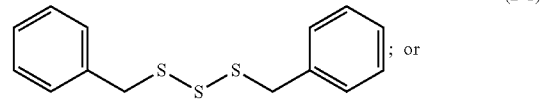

; or (2-1)

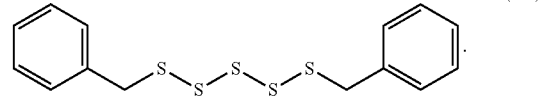

(4-1)

2. A pharmaceutical composition comprising a pharmaceutically acceptable carrier or diluent in combination with a compound according to claim 1.

3. A compound having one of the following structures:

(3-1)
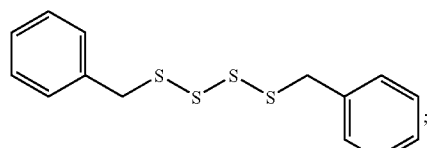

(3-2)
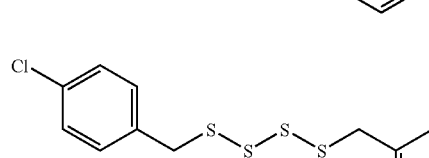

(3-3)

(3-4)
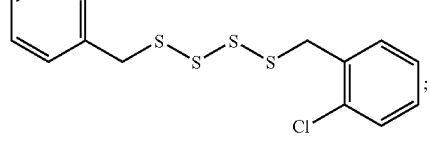

(3-5)
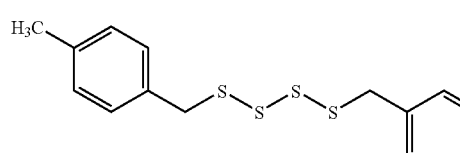

(3-6)

(3-9)
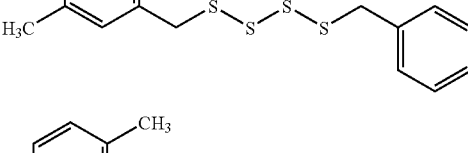

(3-10)
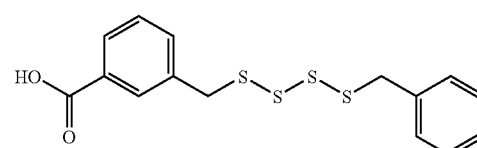

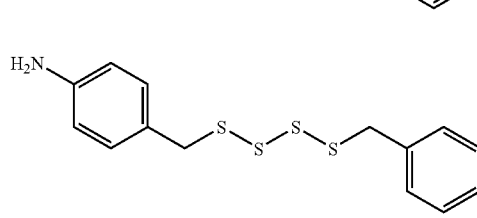

-continued (3-24)
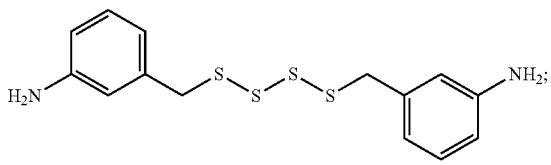

(3-25)
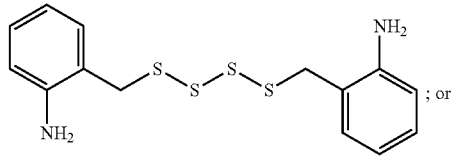
; or (3-23)
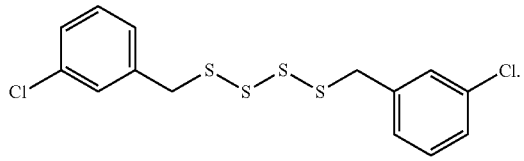

4. The compound of claim 3, wherein the compound has one of the following structures (3-1) or (3-5):

(3-1)
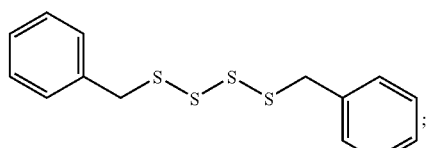
; or (3-5)
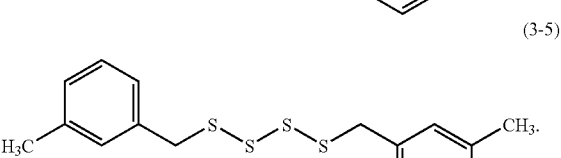

5. A pharmaceutical composition comprising a pharmaceutically acceptable carrier or diluent in combination with a compound according to claim 3.

6. A compound selected from the following structures:

(3-3)
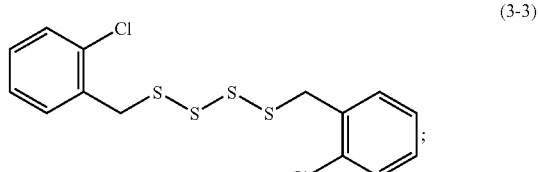

(3-5)
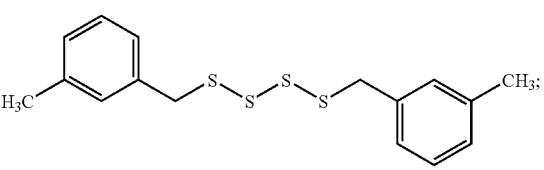

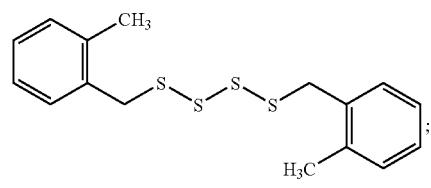
(3-6)
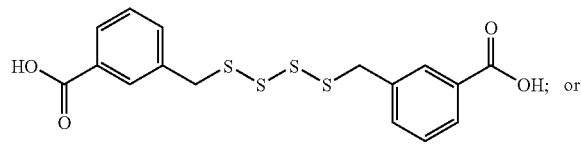
(3-9)
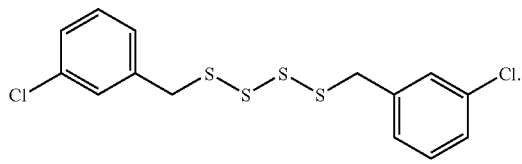
(3-23)
7. A pharmaceutical composition comprising a pharmaceutically acceptable carrier or diluent in combination with a compound according to claim 6.
* * * * *